United States Patent [19]

Sanchez et al.

[11] Patent Number: 5,489,699
[45] Date of Patent: Feb. 6, 1996

[54] UNSATURATED PEROXIDE COMPOSITIONS, POLYMERIC-PEROXIDES DERIVED THEREFROM AND THEIR USES

[75] Inventors: Jose Sanchez, Erie; Leonard H. Palys, Amherst, both of N.Y.; Daryl L. Stein, Westchester, Ohio; John S. Yormick, Kenmore, N.Y.

[73] Assignee: Elfatochem North America, Inc., Philadelphia, Pa.

[21] Appl. No.: 452,548

[22] Filed: May 25, 1995

Related U.S. Application Data

[62] Division of Ser. No. 196,339, Feb. 9, 1994.

[51] Int. Cl.⁶ .................. C07D 323/00; C07C 409/00
[52] U.S. Cl. .................. 549/352; 568/558; 568/561; 568/563; 568/567; 549/353
[58] Field of Search .................. 549/352, 353; 568/558, 561, 563, 567

[56] References Cited

U.S. PATENT DOCUMENTS

| | | |
|---|---|---|
| 3,536,676 | 10/1970 | Mageli et al. . |
| 3,671,651 | 6/1972 | D'Angelo . |
| 3,763,112 | 10/1973 | Bafford et al. . |
| 3,956,319 | 5/1976 | Sacrini et al. ............ 568/561 |
| 4,119,657 | 10/1978 | Komai et al. . |
| 4,129,700 | 12/1978 | Mageli et al. . |
| 4,180,518 | 12/1979 | Mageli et al. . |
| 4,218,548 | 8/1980 | Mageli et al. . |
| 4,304,882 | 12/1981 | D'Angelo et al. . |
| 4,658,001 | 4/1987 | Kato et al. . |
| 4,855,428 | 8/1989 | Verlaan et al. . |
| 5,011,981 | 4/1991 | Tsuboniwa et al. . |

FOREIGN PATENT DOCUMENTS 1041088   9/1966   United Kingdom .

OTHER PUBLICATIONS

Chem. Abs., 91.58075y, 1979.
Chem. Abs., 92,129658z, 1980.
Chem. Abs., 92,130797a, 1980.
Chem. Abs., 93, 480804, 1980.
Strain, J. Am. Chem. Soc., 72, 1254–1263, 1950.
Chem. Abs., 79, 6548n, 1973.
Chem. Abs., 105, 1732325, 1986.

*Primary Examiner*—Joseph L. Schofer
*Assistant Examiner*—Wu C. Cheng
*Attorney, Agent, or Firm*—Royal E. Bright

[57]   ABSTRACT

Novel unsaturated peroxide compositions of Structure A, $$R-Q-X-R_1 \qquad A$$

[Where the R—Q— grouping contains a polymerizable carbon-carbon double bond, —X— is a direct bond or a connecting diradical and —$R_1$ is a peroxide containing radical all as defined in the Summary of the Invention Section.], polymeric-peroxide compositions derived from them and their uses are disclosed.

14 Claims, No Drawings

UNSATURATED PEROXIDE COMPOSITIONS, POLYMERIC-PEROXIDES DERIVED THEREFROM AND THEIR USES

This is a divisional of copending application(s) Ser. No. 08/196,339 filed on Feb. 9, 1994.

BACKGROUND OF THE INVENTION

1. Field of the Invention

This invention relates to novel unsaturated peroxides, their use as free-radical generators for, (1) polymerizing ethylenically unsaturated monomers, (2) curing unsaturated polyester resins, (3) crosslinking olefin polymers, (4) preparing polymeric peroxides, (5) curing elastomeric compositions, (6) rheological modification of olefin polymers and copolymers, (7) grafting of ethylenically unsaturated monomers onto polymers, and (8) compatibilizing of polymer blends. Compounds and processes for their preparation as well as products and articles of manufacture produced by their use are also contemplated by the invention.

There is a need in the polymer industry for efficient, free-radical crosslinking agents for olefin polymers which give longer scorch times and yet provide faster crosslinking rates. Because of its low melt flow, HDPE must be compounded with peroxides at temperatures where the scorch time is relatively short. If the scorch time is too short, premature crosslinking of HDPE occurs during the peroxide compounding step. This is highly undesirable. In the crosslinking of high density polyethylene (HDPE), the peroxide that is predominantly used for crosslinking is 2,5-dimethyl-2,5-di-(t-butylperoxy)-3-hexyne (available as LUPERSOL®130 from Elf Atochem North America, Inc.). Of all the commercially available organic peroxides, LUPERSOL 130 has the highest 10 hour half-life temperature (131° C.). The 10 hour half-life temperature of an initiator is defined as the temperature at which 50% of the initiator decomposes in 10 hours. Generally, the higher the 10 hour half-life temperature the longer the scorch time at a given temperature.

Although LUPERSOL 130 gives adequate scorch times when compounded into HDPE, polymer producers complain of the noxious decomposition products that LUPERSOL 130 produces during crosslinking of polyethylene. The noxious decomposition products are thought to be derived from the carbon-carbon triple bond in LUPERSOL 130 since a similar peroxide that lacks the carbon-carbon triple bond, 2,5-dimethyl-2,5-di-(t-butylperoxy) hexane, does not produce noxious decomposition products. An efficient polyethylene crosslinking agent which yields lengthened scorch times and produces less noxious decomposition products is needed by the polyethylene crosslinking industry.

A novel unsaturated peroxide of the instant invention, 1,3-dimethyl-3-(t-butylperoxy) butyl methacrylate, satisfied these crosslinking needs and was found to be a more effective HDPE crosslinking agent than was LUPERSOL 130. At 385° F. (196° C.) in HDPE, 1,3-dimethyl-3-(t-butylperoxy)butyl methacrylate was found to be at least as efficient as LUPERSOL 130 on an equivalent basis and was found to give faster crosslinking of HDPE than LUPERSOL 130. It also gave longer scorch times than LUPERSOL 130, hence, it is superior to LUPERSOL 130 for crosslinking of HDPE. Perhaps because of the lack of a carbon-carbon triple bond in the structure of 1,3-dimethyl-3-(t-butylperoxy)butyl methacrylate, generation of noxious decomposition products during crosslinking of polyethylene was not observed.

In recent years most of the new polymeric materials that have been commercialized are polymeric blends and alloys composed of two or more different polymers. The reasons for this trend to commercial development of polymer blends and alloys include the short time required for development and commercialization of these materials, the relatively low cost involved in carrying out the R&D effort needed to develop these materials compared to development of entirely new polymers from monomers, and the ability to develop polymeric blends and alloys that are "tailor made" to meet end use property specifications, hence, they are neither over-engineered nor under-engineered, but are just right.

The polymer property improvements achieved by blending include:

Better processability

Impact strength enhancement

Improved flame retardance

Improved barrier properties

Improved tensile properties

Improved adhesion

Improved melt flow

Enhanced heat distortion temperature (HDT)

Enhanced heat resistance

Improved stiffness

Improved chemical resistance

Improved ultraviolet light stability

The major problem encountered in developing new blends and alloys is the inherent incompatibility or immiscibility of almost all mixtures of two or more polymers. The consequence of incompatibility of polymeric blends and alloys is that they are unstable and, with sufficient time and temperature, form separate phases, thus, physical properties of the polymeric blends and alloys suffer. Generally, resin compounders have found that block and graft copolymers having polymeric segments that are compatible with the individual polymer components of blends and alloys enable formation of blends and alloys having enhanced phase stabilities and physical properties.

Low cost blends and alloys are commercially produced from two or more addition polymers such as blends involving low density polyethylene (LDPE), linear low density polyethylene (LLDPE), high density polyethylene (HDPE) and polypropylene (PP). The compatibility of these low cost blends can be improved by crosslinking with peroxides or by use of compatibilizing block or graft copolymers as mentioned above.

An important use of polymeric-peroxides such as polymers derived from the novel unsaturated peroxides of Structure A (as defined herein below) is their utility in preparing graft copolymers useful for compatibilizing polymeric blends and alloys. The polymeric-peroxides, derived from the novel unsaturated peroxides of Structure A of the instant invention, are effective in the preparation of graft copolymer compositions. Such graft copolymers have utility in compatibilizing polymer blends and alloys.

Discussion of Prior Art

U.S. Pat. No. 4,119,657 discloses OO-t-alkyl O-allyl and O-methallyl monoperoxycarbonates:

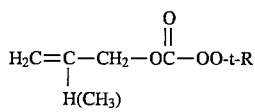

Later publications, Chem. Abstracts, 91, 58075y, abstracting Japanese kokai 79 47,790; Chem. Abstracts, 92, 129658z, abstracting Japanese kokai 79 132,695; Chem. Abstracts, 92, 130797a, abstracting Japanese kokai 79 142, 239; and Chem. Abstracts, 93, 48080y, abstracting Japanese kokai 80 09636 disclose preparations of polymeric peroxides by copolymerizing these OO-t-alkyl O-allyl and O-methallyl monoperoxycarbonates with ethylenically unsaturated monomers and preparations of graft copolymers from the resulting polymeric peroxides. These peroxides and the polymeric peroxides derived from them are not covered by the novel unsaturated peroxides of Structure A and the corresponding novel polymeric-peroxides derived from the compositions of Structure A.

F. Strain, J. Am. Chem. Soc., 72, PP. 1254–1263 (1950) disclosed low temperature dialkyl peroxydicarbonates and reported the preparation of diallyl peroxydicarbonate, a peroxydicarbonate with allyl groups. Based on data in this paper the latter peroxydicarbonate was very hazardous and exploded.

Chem. Abstracts, 79, 6548n, abstracting Italian Patent 869,166 discloses unsaturated diperoxide compounds for vulcanization of ethylene-propylene rubber, such as 1-phenyl-3,3 -di-(t-butylperoxy)-1-propene:

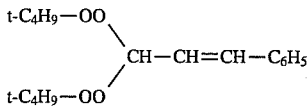

The latter is not expected to polymerize very readily owing to the presence of a substituent on each of the unsaturated carbons. The structures of this Italian Patent are not covered by Structure A of the instant invention.

U.S. Pat. No. 3,536,676 discloses di-t-alkyl diperoxyfumarates and the copolymerizations of these diperoxyfumarates with monomers such as styrene, vinyl acetate, vinyl chloride, acrylonitrile, methyl methacrylate and butadiene.

U.S. Pat. No. 3,763,112 discloses the preparations of di-t-alkyl diperoxyfumarate adducts (polymeric and non-polymeric) that are preparable via reaction of di-t-alkyl diperoxyfumarate with compounds possessing labile C—H bounds, in the presence or absence of conventional free-radical generators and or upon exposure to actinic light (visible, ultraviolet, etc.).

Chem Abstracts, 105(20), 173232s, abstracting Japanese Patent Application 84/209679 discloses various OO-t-alkyl O-alkyl monoperoxyfumarates and the use of these monoperoxyfumarates in the preparation of styrene polymers of enhanced moldability.

British Patent 1,041,088 discloses peroxide-containing copolymer compositions derived from ethylenically unsaturated monomers such as vinyl esters, esters of (meth-)acrylic acid, vinyl chloride, acrylonitrile, butadiene, isoprene, acrylamide and vinyl ethers, and unsaturated peroxyesters such as t-butyl peroxymethacrylate, OO-t-butyl O-hydrogen monoperoxymaleate, OO-t-butyl O-butyl monoperoxymaleate, OO-t-butyl O-butyl monoperoxyfumarate and t-butyl peroxycinnamate. In the cases of the OO-t-alkyl O-hydrogen monoperoxy fumarates and the OO-t-alkyl O-hydrogen monoperoxymaleates, polymers produced from them are expected to react at elevated temperatures via non-radical reactions to form non-peroxidic polymers and t-alkyl hydroperoxides. t-Butyl peroxymethacrylate is difficult to prepare and is hazardous owing to very exothermic self polymerization/decomposition. t-Butyl peroxycinnamate does not homopolymerize nor copolymerize very readily with common polymerizable ethylenically unsaturated monomers.

U.S. Pat. No. 4,658,001 discloses polymerizable, ethylenically unsaturated monoperoxycarbonates of Structure Z.

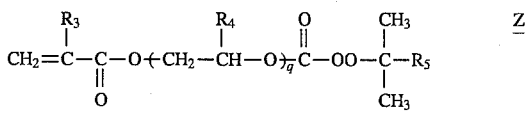

and copolymers derived therefrom. Peroxide compounds of Structure Z are not covered by the unsaturated peroxide compositions of Structure A.

U.S. Pat. No. 4,855,428 discloses triazine peroxides possessing at least one carbon-carbon double bond, for instance, 2-t-amylperoxy-4,6-dialloxy-1,3,5-triazine, which are useful for crosslinking polymers and copolymers derived from ethylene. These compositions are not covered by Structure A of the instant invention and are not expected to polymerize very readily.

U.S. Pat. No. 4,129,700, U.S. Pat. No. 4,180,518, and U.S. Pat. No. 4,218,548 claim peroxides of the general formula:

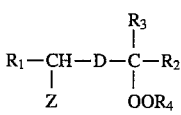

where $R_1$ is hydrogen or an alkyl radical of 1 to 4 carbons, $R_2$ and $R_3$ are alkyl radicals of 1 to 4 carbons, $R_4$ is a t-alkyl radical of 4 to 8 carbons, and Z is,

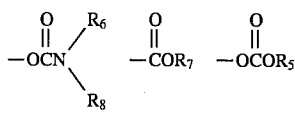

where $R_5$ and $R_7$ are alkyl radicals of 1 to 8 carbons, $R_6$ and $R_8$ are hydrogen, alkyl radicals of 1 to 8 carbons, cycloalkyl radicals of 5 to 6 carbons, phenyl radicals, or alkylphenyl radicals of 7 to 10 carbons, and where D is an ethynyl diradical, a diethynyl diradical, or an alkyl diradical having 1 to 8 carbons. An example of a peroxide covered under these patents would be the reaction product of 2-(t-butylperoxy)-2-methyl-4-hydroxypentane with cyclohexyl isocyanate. This compound does not have a pendent polymerizable vinyl group. Moreover, as can be seen from the general structure given by these patents, in no case is there a compound claimed with a pendent polymerizable vinyl group as described by our general formula. However, another compound, whose synthesis is described in all three patents but which is not claimed, is the reaction product of allyl amine and 2-(t-butylperoxy)-2-methyl-4-chlorocarbonyloxypentane, i.e., N-allyl-O-[2-(t-butylperoxy)-2-methyl-4-pentyl]carbamate. Although this peroxide contains an allyl group, it is outside the scope of our invention as described by our general formula, because for the above carbamate to be covered by the instant invention —X— would have to be the connecting diradical, —CH$_2$NH—. This connecting diradical is not one of the definitions for —X— of Structure A.

U.S. Pat. No. 3,671,651 and U.S. Pat. No. 4,304,882 broadly disclose polymers with attached peroxide groups.

However, these peroxy polymers were produced by the reaction of a peroxychloroformate such as 2-(t-butylperoxy)-2-methyl-4-chlorocarbonyloxypentane and a hydroxy containing polymer such as a polyether diol (for example, Carbowax™ produced by the Union Carbide Corp.). In general, U.S. Pat. No. 3,671,651 teaches that a peroxide with an acylating functionality such as an acid chloride or a chloroformate can react with polymers containing terminal or pendent hydroxyl, amino, and mercapto groups or any other functionality that can be acylated. This patent specifically claims peroxy polymers in which the peroxide is attached to the polymer by either an ester or a carbonate group (i.e. connecting groups), there is no claim of either an amide, a carbamate, or a urea as connecting groups which by definition are part of general structure A of our invention. Moreover, there is no mention that peroxy polymers can be prepared by copolymerization with a peroxy monomer. Therefore, the peroxy polymers of U.S. Pat. No. 3,671,651 are outside the scope of this invention. U.S. Pat. No. 4,304,882 also teaches that peroxides with acylating functionalities can react with polymers containing terminal or pendent hydroxyl, amino, or mercapto groups to form peroxy polymers. In this case amide and carbamate groups are specifically claimed as connecting groups linking the peroxide moiety to the polymer backbone. However, there is no mention of vinyl group containing peroxy monomers being copolymerized with other monomers or of the peroxide being part of the repeat unit(s) in the polymer backbone. In addition there is a difference in the general formulas for this patent and our invention. The general formula for the peroxy polymers of U.S. Pat. No. 4,304,882 is as follows:

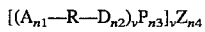

where: n1, n2, n3, n4, v, and w are integers; A defines a peroxide moiety; R is a di-, tri-, or tetra valent hydrocarbon radical; D is an ester, carbonate, amide, carbamate, etc. connecting group; P is a polyvalent residue of a polymer less its terminal and pendent Z and ($A_{n1}$—R—$D_{n2}$) groups; and Z is —H, —OH, —$NH_2$, etc. Thus, in the case of the general formula in U.S. Pat. No. 4,304,882, the —R—D— group connects the peroxide unit, A-, to the polymer backbone. In the general formula A for the compositions of the instant invention the connecting group between the polymer backbone and the peroxide group, —$R_1$, is —X—. The definitions of —X— are different than those of —R—D. For instance, in the case of the peroxy-polymers of U.S. Pat. No. 4,304,882, the connecting group of atoms to the polymer backbone is either —O—(P)—, —NH—(P)—, —$NR_2$—(P)— or —S—(P)— [Where (P) is a polymer backbone of U.S. Pat. No. 4,304,882.]. In the case of the instant invention the connecting group of atoms to the polymer backbone is either one or more carbon atoms, —C(O)—(P')— or —O—C(O)—(P')— [where (P') is a polymer backbone of the instant invention.] Thus, in the instant invention the peroxide is attached to the polymer backbone by quite different connecting groups.

U.S. Pat. No. 5,011,981 discloses the reaction products of methacryloyl isocyanate and hydroperoxides. A typical example is the reaction of t-butyl hydroperoxide with methacryloyl isocyanate to yield a peroxycarbamate with the following proposed structure:

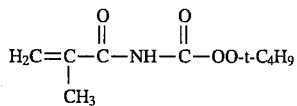

Although this is a polymerizable peroxide, it is outside the scope of our invention, because for it to be included in our invention, —X— of our general structure would have to be the connecting diradical, —C(O)—NH—. This connecting diradical is not included in the definition of —X—.

SUMMARY OF THE INVENTION

This invention provides in a first composition aspect novel ethylenically unsaturated peroxide compositions of Structure A:

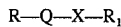   A where:

Q is an unsaturated diradical selected from structures (1), (2), or (3)

   (1)

   (2)

   (3)

where (X—$R_1$) shows the point of attachment of the X—$R_1$ group and (R) shows the point of attachment of the R group to the Q diradical;

R is selected from the group consisting of H—, carboxy, alkoxycarbonyl radicals of 2 to 19 carbons, aryloxycarbonyl radicals of 7 to 15 carbons, t-alkylperoxycarbonyl radicals of 5 to 11 carbons, alkyl radicals of 1 to 18 carbons, alkenyl radicals of 2 to 18 carbons, aryl radicals of 6 to 10 carbons, and $R_1$—X— radicals;

$R_2$ is selected from the group consisting of H— and alkyl radicals of 1 to 4 carbons;

$R_3$ is selected from the group consisting of H—, alkyl radicals of 1 to 18 carbons and alkenyl radicals of 2 to 18 carbons provided that when $R_3$ is methyl, R and $R_2$ are not both hydrogen;

$R_1$ is a peroxy containing radical of structures (4), (5), and (6):

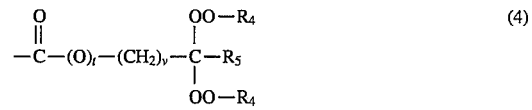   (4)

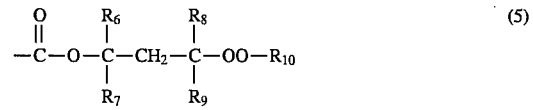   (5)

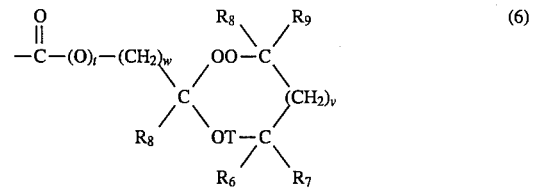   (6)

where:

t is 0 or 1;

v is 1 or 2;

w is 1 or 2;

T is a direct bond or oxy;

$R_4$ is selected from the group consisting of t-alkyl radicals of 4 to 12 carbons, t-aralkyl radicals of 9 to 13 carbons and t-alkynyl radicals of 5 to 9 carbons;

$R_5$, $R_8$ and $R_9$ are the same or different and are selected from the group consisting of alkyl radicals of 1 to 4 carbons;

in structure (5) and when T is a direct bond in structure (6), $R_6$ and $R_7$ are the same or different and are selected from the group consisting of H— and alkyl radicals of 1 to 4 carbons;

in structure (6) when T is oxy, $R_6$ and $R_7$ are the same or different and are selected from the group consisting of alkyl radicals of 1 to 4 carbons;

$R_{10}$ is selected from the group consisting of t-alkyl radicals of 4 to 12 carbons, t-aralkyl radicals of 9 to 13 carbons, t-alkynyl radicals of 5 to 9 carbons, and structures (7), (8), (9), (10), (11) and (12):

(7)

(8)

(9)

(10)

(11)

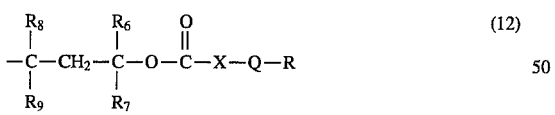

(12)

where:

$R_{12}$ and $R_{13}$ can be the same or different and are selected from the group consisting of H— and alkyl radicals of 1 to 8 carbons;

$R_{14}$ is selected from the group consisting of H—, alkyl radicals of 1 to 8 carbons, alkenyl radicals of 2 to 8 carbons, aryl radicals of 6 to 10 carbons, alkoxy radicals of 1 to 6 carbons, and aryloxy radicals of 6 to 10 carbons;

$R_{13}$ and $R_{14}$ may be concatenated to form an alkylene diradical of 4 to 5 carbons;

$R_{15}$ and $R_{16}$ are independently selected from alkyl radicals of 1 to 4 carbons;

$R_{17}$ and $R'_{17}$ are independently selected from the group consisting of H—, lower alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, hydroxy, fluoro, chloro, and bromo;

x is 0 or 1;

$R_{18}$ is selected from substituted or unsubstituted alkyl radicals of 1 to 18 carbons, substituents being one or more alkyl radicals of 1 to 6 carbons, t-alkylperoxy radicals of 4 to 8 carbons, alkoxy radicals of 1 to 6 carbons, aryloxy radicals of 6 to 10 carbons, hydroxy, chloro, bromo and cyano; substituted or unsubstituted cycloalkyl radicals of 5 to 12 carbons, substituted or unsubstituted saturated heterocycles of 5 to 12 atoms having an oxygen atom or a nitrogen atom in the heterocyclic ring with substituents for either cyclic radical being one or more lower alkyl radicals of 1 to 4 carbons, or $R_{18}$ may optionally be the radical:

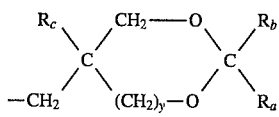

where y is 0 or 1, $R_a$, $R_b$ and $R_c$ are the same or different and are selected from H— or alkyl radicals of 1 to 8 carbons, with the proviso that $R_a$ and $R_b$ may be concatenated to form a substituted or unsubstituted alkylene diradical of 4 to 11 carbons, with substituents being one or more alkyl radicals of 1 to 5 carbons or phenyl radicals;

$R_{19}$ is selected from the group consisting of alkyl radicals of 1 to 4 carbons and, additionally, the two $R_{19}$ radicals may optionally be concatenated to form an alkylene diradical of 4 to 5 carbons;

$R_{11}$ is selected from the group consisting of unsubstituted alkylene diradicals of 2 to 3 carbons, alkylene diradicals of 2 to 3 carbons substituted with one or more alkyl radicals of 1 to 4 carbons, an unsubstituted 1,2-phenylene diradical, and 1,2-phenylene diradicals substituted with one or more lower alkyl radicals of 1 to 4 carbons, chloro, bromo, nitro or carboxy; and, X is a direct bond or is selected from the group consisting of connecting diradical structures (13), (14), (15) and (16):

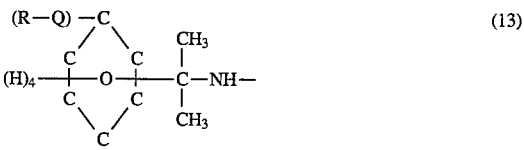

(13)

(14)

(15)

(16)

where (R—Q) shows the point of attachment of the R—Q group to the unsymmetrical X connecting diradical;

z is 1 to 10;

$R_{22}$ is an alkylene diradical of 2 to 4 carbons, optionally substituted with one or more alkyl radicals of 1 to 4 carbons; and, when the X connecting diradical is structure (16), $R_1$ may additionally be the peroxide containing radical of structure (17):

The tangible embodiments of the first composition aspect of the invention possess infrared spectrographic, gas and liquid chromatographic and differential scanning calorimetric properties positively confirming the structures sought to be patented.

The invention provides in a second composition aspect, novel polymeric peroxides derived from the novel polymerizable ethylenically unsaturated peroxides of the first composition aspect of the invention of structure A, such polymeric peroxides possessing recurring units selected from structures B, C, or D:

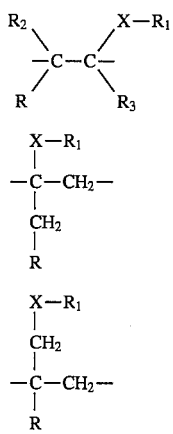

where R, $R_1$, $R_2$, $R_3$ and X have the definitions provided hereinabove in the description of the first composition aspect of the invention.

The tangible embodiments of the second composition aspect of the invention possess infrared spectrographic, gel permeation chromatographic, liquid chromatographic, extractive as well as differential scanning calorimetric properties which positively confirm the structures sought to be patented.

The invention provides in a first process aspect, a process for the use of peroxides of the first composition aspect of the invention as free radical initiators in amounts effective for the initiation of free radical reactions selected from among the group of free radical reactions consisting of:

a) curing unsaturated polyester resin substrates,
b) polymerizing ethylenically unsaturated monomer substrates,
c) crosslinking olefin polymer substrates,
d) curing of elastomer substrates,
e) modifying polyolefin substrates,
f) grafting ethylenically unsaturated monomer substrates onto olefin homo- and copolymer substrates, and
g) compatibilizing blends of two or more normally incompatible polymer substrates; which comprises heating said substrates in the presence of an amount effective for initiating the reaction to be performed of one or more peroxides of the first composition aspect of the invention for a time sufficient to at least partially decompose said peroxides of the first composition aspect of the invention.

The invention provides in a second process aspect, the use of peroxides of the first composition aspect of the invention in forming the peroxy polymers of the second composition aspect of the invention which comprises heating one or more peroxides of the first composition aspect of the invention, in the presence or absence of one or more other free radical polymerizable ethylenically unsaturated monomers, in the presence of an amount effective for initiating free radical reactions of a lower temperature conventional free radical initiator for a time sufficient to at least partially decompose said lower temperature conventional initiator.

The invention provides in a third process aspect, a process for the use of peroxy polymers of the second composition aspect of the invention in compatibilizing two or more otherwise incompatible polymers which comprises;

a) decomposing at least one peroxy polymer of the second composition aspect of the invention in the presence of a substrate selected from the group consisting of free radical poloymerizable monomers and free radical curable polymers to form a copolymer, b) incorporating a compatibilizing effective amount of the copolymer formed in step a above into a mixture of two or more otherwise incompatible polymers each member of which polymer mixture is compatible with at least one of the polymeric portions of said copolymer formed in step a.

The invention provides in a fourth process aspect, a process for the use of peroxides of the first composition aspect of the invention in compatibilizing two or more otherwise incompatible polymers which comprises decomposing a compatibilizing effective amount of a peroxide of the first composition aspect of the invention in the presence of a mixture of two or more normally incompatible polymers.

The invention provides in a third composition aspect, the products produced by the process of the first process aspect of the invention.

The invention provides in a fourth composition aspect, as articles of manufacture, the products produced by the third process aspect of the invention.

The invention provides in a fifth composition aspect, as articles of manufacture, the products produced by the fourth process aspect of the invention.

DETAILED DESCRIPTION

The preferred manner of using and making the embodiments of the invention is detailed specifically as follows:

Utility of the Novel Unsaturated Peroxides of The First Composition Aspect of The Invention A. Polymerization of Ethylenically Unsaturated Monomers In the free-radical polymerizations of ethylenically unsaturated monomers at suitable temperatures and pressures, the novel unsaturated peroxides of Structure A of this invention were found to be effective initiators with respect to efficiency (reduced initiator requirements, etc.). Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate diethylene glycol bis(allyl carbonate) (i.e., ADC); acrolein; methyl vinyl ketone; and mixtures thereof.

Temperatures of 0° C. to 250° C., preferably 30° C. to 200° C., are normally employed in conventional polymerizations and copolymerizations of ethylenically unsaturated monomers.

Amounts effective for the initiation of free radicals in polymerization and copolymerization reactions of ethylenically unsaturated monomers are levels of concentration by weight based on monomers of the unsaturated peroxide compositions of the first composition aspect of the invention (on a pure basis) of from 0.002% to 3%, preferably from 0.005% to 1%, and more preferably from 0.01% to 0.75%.

The unsaturated peroxides of this invention can be used in combination with other free-radical initiators such as those disclosed at the bottom of column 4 and the top of column 5 of U.S. Pat. No. 4,525,308 as non-invention free-radical initiators. Using the unsaturated peroxides in combination with these initiators adds flexibility to the processes of polymer producers and allows them to "fine tune" their polymerization processes. Mixtures of two or more unsaturated peroxides can also be used where appropriate.

B. Curing of Unsaturated Polyester Resins

In the curing of unsaturated resin compositions by heating at suitable curing temperatures in the presence of free-radical curing agents, the unsaturated peroxides of Structure A of this invention exhibit enhanced curing activity in the curable unsaturated polyester resin compositions. Unsaturated polyester resins that can be cured by the unsaturated peroxides of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2-and 1,3-propanediols, 1,2-, 1,3- and 1,4-butanediols, 2,2-dimethyl-1,3-propanediol, 2-hydroxymethyl-2-methyl-1, 3-propanediol, 2-buten-1,4-diol, 2-butyn-1,4-diol, 2,4,4-trimethyl-1,3pentanediol, glycerol, pentaerythritol, mannitol and others. Mixtures of such di- or polyacids and/or mixtures of such di- or polyols may also be used. The di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2, 3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others which are copolymerizable with said unsaturated polyesters. Mixtures of the ethylenically unsaturated monomers may also be employed.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene.

Other types of unsaturated polyester resin compositions can be cured using the unsaturated peroxides of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with appropriate amounts of a bisphenol such as Bisphenol A [2,2-(4-hydroxyphenyl)propane], in the presence of a base, such as sodium hydroxide, to yield a condensation product having terminal epoxy groups derived from the chloroepoxide. Subsequent reaction of the condensation products with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. are normally employed.

Amounts effective for the initiation of free radicals in curing of unsaturated polyester resins are levels of concentration by weight based on resin of the unsaturated peroxide compositions of the first composition aspect of the invention (on a pure basis) of about 0.05% to 5% or more, preferably 0.10% to 4%, more preferably 0.20% to 3%.

The unsaturated polyester resin compositions described above can be filled with various materials, such as sulfur, glass, carbon and boron fibers, carbon blacks, silicas, metal silicates, clays, metal carbonates, antioxidants (AO's), heat, untraviolet (UV) and light stabilizers, sensitizers, dyes, pigments, accelerators, metal oxides, such as zinc oxide, blowing agents, nucleating agents and others.

C. Curing of Elastomers and Crosslinking of Thermoplastic Polymers

In the curing of elastomeric compositions, and the crosslinking of polymer compositions, by heating at suitable curing and crosslinking temperatures in the presence of free-radical curing and crosslinking agents, the unsaturated peroxides of Structure A of this invention exhibit curing and crosslinking activities.

Elastomeric resin compositions that can be cured by the unsaturated peroxides of this invention include elastomers such as ethylene-propylene copolymers (EPR), ethylene-propylene-diene terpolymers (EPDM), polybutadiene (PBD), silicone rubber (SR), nitrile rubber (NR), neoprene, fluoroelastomers and ethylene-vinyl acetate copolymer (EVA).

Polymer compositions that can be crosslinked by the unsaturated peroxides of this invention include olefin thermoplastics such as chlorinated polyethylene (CPE), low density polyethylene (LDPE), linear-low density polyethylene (LLDPE), and high density polyethylene (HDPE). Other crosslinkable thermoplastic polymers include poly(vinylchloride) (PVC), polystyrene, poly(vinyl acetate), polyacrylics, polyesters, polycarbonate, etc.

Temperatures of about 80° C. to 310° C. are normally employed.

Amounts effective for the initiation of free radicals in curing of elastomers and crosslinking of thermoplastic polymers are levels of concentration by weight based on uncured or uncrosslinked resin of the unsaturated peroxide compositions of the first composition aspect of the invention (on a pure basis) of from 0.1 to 10%, preferably 0.5% to 5%, more preferably 0.5 to 3%.

The curable elastomeric resin composition or crosslinkable polymer composition can be optionally filled with the materials listed above for use with the conventional unsaturated polyester resin compositions.

D. Modification of Polyolefins and Other Polymers

In the processes for modifying polyolefins [e.g., beneficial degradation of polypropylene (PP) by reducing the polymer molecular weight and reducing the polymer molecular weight distribution and enhancing the molecular weight and film forming properties of linear low density polyethylene (LLDPE)] and copolymers, the unsaturated peroxides of Structure A of this invention exhibit polyolefin modification activity. Other polymers that can be modified with unsaturated peroxides include HDPE, ethylene-propylene copolymer, etc.

Temperatures of about 140° C. to 340° C. are normally employed.

Amounts effective for the initiation of free radicals in the modification of polyolefins and other polymers are levels of concentration by weight based on unmodified polyolefin or other unmodified polymer of unsaturated peroxide compositions of the first composition aspect of the invention (on a pure basis) of about 0.001% to 1.0%, preferably 0.01% to 1%, more preferably 0.01% to 0.5%.

Optionally, up to 1% by weight of molecular oxygen can be employed as a modification co-catalyst.

Utility of Polymeric Peroxide Derivatives of the Second Composition Aspect of the Invention The novel polymeric peroxides of the second composition aspect of the invention have utility in several applications. They can be used to prepare block and graft copolymers by several techniques. A graft copolymer of the polymeric peroxide derivative can be made by using the polymeric peroxide derivative as the backbone polymer as well as the initiator, and grafting monomers onto this backbone. A graft copolymer containing two or more monomers that are not the same as the monomer(s) of Structure A in a particular polymeric peroxide of the second composition aspect of the invention can be made by partially decomposing the polymeric peroxide first in the presence of one monomer followed by decomposing in the presence of a second monomer, etc. The grafting processes can be carried out in solution or in polymer processing equipment such as extruders. Such graft copolymers have utility in compatibilizing homopolymer and copolymer blends and alloys.

The polymeric peroxides of the second composition aspect of the invention can also be used in reactive processing to compatibilize polymers in situ by forming block and graft copolymers in polymer processing equipment such as extruders, roll mills, etc.

The polymeric peroxides of the second composition aspect of the invention can also be used to enhance the quality of interpenetrating polymer networks (IPN's) in polymer processing equipment.

Polymeric peroxides of the second composition aspect of the invention can be used in reactive processing to enhance the impact resistance of polymer blends.

The polymeric peroxides of the second composition aspect of the invention also have utility as polymeric low profile/low shrink curing agents, as self-curing polymeric systems and as self degrading polymer systems.

Finally, the polymeric peroxides of the second composition aspect of the invention are the ultimate in polymer-peroxide master batches (i.e., polymer-peroxide composition with up to 5% or more of organic peroxides, useful in crosslinking, curing and polymer modification applications) since the peroxide functions are compatible with the polymer backbone (covalently attached) and cannot bloom, exude or volatilize.

Preparations of the Novel Unsaturated Peroxides of Structure A

Several synthetic methods can be used for preparations of the novel unsaturated peroxides of Structure A. One method is to react a hydroxy substituted peroxide with an unsaturated acid halide, an unsaturated haloformate or an unsaturated cyclic acid anhydride in the presence of a suitable base and an optional solvent. Suitable bases include triethylamine, tributylamine, N,N-dimethylaniline, urea, tetramethylurea, sodium hydroxide, sodium carbonate, sodium hydrogen carbonate, potassium hydroxide, potassium carbonate, potassium hydrogen carbonate, calcium hydroxide, barium hydroxide, calcium carbonate and trisodium phosphate. Reaction of hydroxy substituted peroxides with unsaturated cyclic anhydrides can take place in the presence of a strong organic or strong inorganic acid. Suitable strong organic or strong inorganic acids include methanesulfonic acid, benzenesulfonic acid, toluenesulfonic acid, sulfuric acid, sodium hydrogen sulfate, potassium hydrogen sulfate, perchloric acid, nitric acid, hydrochloric acid, phosphoric acid, and mixtures thereof.

Another synthetic route to the unsaturated peroxides of Structure A involves reaction of a hydroxy substituted peroxide with an unsaturated isocyanate with or without an optional solvent and preferably in the presence of a suitable catalyst, such as an alkyltin salt, for instance, dibutyltin dilaurate.

Another synthetic route to the unsaturated peroxides of Structure A involves reaction of an unsaturated ketone with a t-alkyl hydroperoxide in the presence of a strong organic or inorganic acid.

Yet another synthetic route to certain unsaturated peroxides of Structure A involves reaction of certain unsaturated hydroxy compounds of the structures:

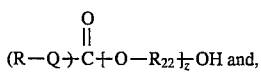

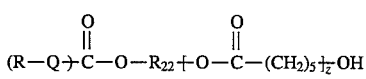

with certain peroxides with haloformate groups, in the presence of suitable bases and optional solvents, to form unsaturated peroxides of the structures:

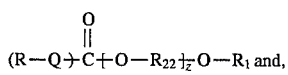

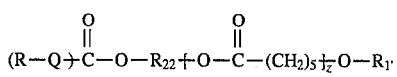

respectively.

A specific synthetic route to certain unsaturated peroxides of Structure A involves reaction of an unsaturated haloformate of the structure:

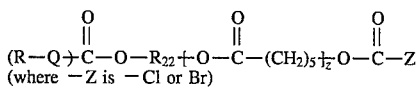
(where —Z is —Cl or Br)

with a t-alkyl hydroperoxide in the presence of suitable bases and optional solvents, to form an unsaturated peroxide of the structure:

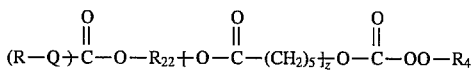

Hydroxy substituted peroxides that may be used for the preparations of the novel unsaturated peroxides of Structure A, can be prepared by methods well known in the art (U.S. Pat. No. 3,236,872, U.S. Pat. No. 4,525,308, and European Patent Application 0381135 A2). Non-limiting examples of hydroxy substituted peroxides include, 2-(t-butylperoxy)-2-methyl-4-hydroxypentane, 2-(t-amylperoxy)-2-methyl-4-hydroxypentane, 2-(t-butylperoxy)-2-methyl-4-hydroxybutane, 2-(t-amylperoxy)-2-methyl-4-hydroxybutane, OO-t-butyl O-(2-hydroxyethyl) monoperoxysuccinate, OO-t-butyl O-(2-hydroxyethyl) monoperoxyphthalate, 3-hydroxy-1,1-dimethylbutyl peroxy-2-methylbenzoate, 2-methoxy-2-(3-hydroxy-1,1-dimethylbutylperoxy)propane 3-hydroxy-1,1-dimethylbutyl peroxy-2-ethylhexanoate, 3-hydroxy-1,1-dimethylbutyl peroxyacetate, 3-hydroxy-1,1-dimethylbutyl peroxyisobutyrate, 3-hydroxy-1,1-dimethylbutyl peroxyneoheptanoate, and, di-(3-hydroxy-1,1-dimethylbutyl) peroxide.

Non-limiting examples of peroxides possessing haloformate groups, which are reactive with certain unsaturated alcohols, include, 1,3-dimethyl-3-(t-butylperoxy)butyl chloroformate, 3-methyl-3-(t-butylperoxy)butyl chloroformate, 1,3-dimethyl-3-(t-amylperoxy)butyl chloroformate, 3-methyl-3-(t-amylperoxy) butyl chloroformate, 1,3-dimethyl-3-(2-ethylhexanoylperoxy)butyl chloroformate, 1,3-dimethyl-3-(neoheptanoylperoxy)butyl chloroformate, 1,3-dimethyl-3-(neodecanoylperoxy)butyl chloroformate, 3,3-di-(t-butylperoxy)butyl chloroformate, 1,3-dimethyl-3-(2-methylbenzoylperoxy)butyl chloroformate and di-(1,3-dimethyl-3-chlorocarbonyloxybutyl) peroxide.

These haloformate containing peroxides can be prepared by reacting the corresponding hydroxy substituted peroxides with excess carbonyl dihalide (e.g., phosgene) under conditions effective for formation of the haloformate.

Non-limiting examples of t-alkyl hydroperoxides which can be used in the synthetic processes for preparing certain unsaturated peroxides of Structure A, include, t-butyl hydroperoxide, t-amyl hydroperoxide, t-hexyl hydroperoxide, 1,1,3,3-tetramethylbutyl hydroperoxide, cumene hydroperoxide, 3-hydroxy-1,1-dimethylbutyl hydroperoxide, 1-methylcyclohexyl hydroperoxide and 3-methyl-3-hydroperoxy-1-butyne.

Non-limiting examples of certain unsaturated hydroxy compounds that are reactive with peroxides containing haloformate groups, include, 2-hydroxyethyl acrylate, 2-hydroxypropyl acrylate, 2-hydroxyethyl methacrylate, 2-hydroxypropyl methacrylate, 2-hydroxyethoxyethyl acrylate and TONE™ 100. (TONE 100 is a hydroxy acrylate monomer of the structure:

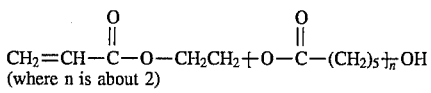
(where n is about 2)

which is manufactured by the Union Carbide Corporation.)

Non-limiting examples of unsaturated acid halides, haloformates and cyclic anhydrides that can be reacted with hydroxy substituted peroxides to form the novel unsaturated peroxides of Structure A, include, acryloyl chloride, methacryloyl chloride, 2-acryloxyethyl chloroformate, 2-methacryloxyethyl chloroformate, 2-acryloxypropyl chloroformate, fumaryl chloride, alkyl fumaryl chlorides (such as ethyl fumaryl chloride) maleic anhydride, itaconic acid anhydride and TONE 100 chloroformate.

Non-limiting examples of unsaturated isocyanates that can be reacted with hydroxy substituted peroxides to form the novel unsaturated peroxides of Structure A, include, isocyanatoethyl methacrylate, 1-(1-isocyanato-1-methylethyl)-3-(1 methylethenyl)benzene, and 1-(1-isocyanato-1-methylethyl)-4-(1-methylethenyl)benzene.

Non-limiting examples of unsaturated ketones that can be reacted with hydroperoxides and strong organic and inorganic acids to form certain novel unsaturated diperoxyketals of Structure A, include, 2-acetoacetoxyethyl acrylate and 2-acetoacetoxyethyl methacrylate.

Non-limiting examples of optional solvents useful for and in the preparation of the novel unsaturated peroxides (Structure A) of this invention include pentane, hexanes, heptanes, dodecanes, odorless mineral spirits mixtures, toluene, xylenes, cumene, methylene chloride, ethyl acetate, 2-ethylhexyl acetate, isobutyl isobutyrate, dimethyl adipate, dimethyl succinate, dimethyl glutarate (or mixtures thereof), dimethyl phthalate, dibutyl phthalate, benzyl butyl phthalate, diethyl ether, methyl t-butyl ether, 2-methoxyethyl acetate and others.

Non-limiting examples of the novel unsaturated peroxides of Structure A, in addition to those in the examples, include the following:
ethyl 1,3-dimethyl-3-(t-amylperoxy)butyl fumarate,
di-[1,3-dimethyl-3-(t-amylperoxy)butyl] fumarate,
1,3-dimethyl-3-(t-amylperoxy)butyl hydrogen maleate,
3-methyl-3-(t-butylperoxy)butyl methacrylate,
3-methyl-3-(t-butylperoxy)butyl acrylate,
1,3-dimethyl-3-(t-amylperoxy)butyl methacrylate,
1,3-dimethyl-3-(t-amylperoxy)butyl acrylate,
3-methyl-3-(t-amylperoxy)butyl methacrylate,
3-methyl-3-(t-amylperoxy)butyl acrylate,
1,3-dimethyl-3-(2-ethylhexanoylperoxy)butyl methacrylate,
1,3-dimethyl-3-(2-ethylhexanoylperoxy)butyl acrylate,
1,3-dimethyl-3-(neoheptanoylperoxy)butyl methacrylate,
1,3-dimethyl-3-(neodecanoylperoxy)butyl acrylate,
1,3-dimethyl-3-(2-methylbenzoylperoxy)butyl methacrylate,
1,3-dimethyl-3-(2-methylbenzoylperoxy)butyl acrylate, and
di-(3-acryloyloxy-1,1-dimethylbutyl) peroxide.

Preparations of the Novel Polymeric-Peroxides of
The Second Composition Aspect of The Invention Novel polymeric-peroxides derived from the novel polymerizable, unsaturated peroxide compositions of Structure A, can be prepared such that the polymeric-peroxides produced possess recurring units selected from Structures B, C and D as set forth herein above.

In general, the novel unsaturated peroxides of the instant invention can be homopolymerized under self-initiating conditions or with non-invention free-radical initiators under conditions effective for initiating polymerization of the novel unsaturated peroxides of Structure A, thus producing novel polymeric peroxides possessing pendant peroxide groups. The novel unsaturated peroxides of the instant invention can also be copolymerized with co-monomers under similar conditions to produce novel copolymeric peroxides possessing pendant peroxide groups.

Non-limiting examples of co-monomers that may be copolymerized with the novel unsaturated peroxides of this invention to produce novel polymeric peroxides, include, ethylene, propylene, butadiene, isoprene, chloroprene, vinyl chloride, acrylonitrile, styrene, alpha-methylstyrene, p-methylstyrene, methyl acrylate, ethyl acrylate, butyl acrylate, butyl methacrylate, 2-hydroxyethyl methacrylate, 2-ethylhexyl methacrylate, methyl methacrylate, acrylamide, acrylic acid, methacrylic acid, maleic anhydride, ethyl vinyl ether, vinyl acetate, acrolein, glycidyl vinyl ether, and mixtures thereof.

Non-limiting, non-invention free-radical initiators useful for initiating homo- and copolymerizations of the novel unsaturated peroxides of Structure A include; peroxyesters such as, t-butyl peroxyacetate, t-butyl peroxy-3,5,5-trimethylhexanoate, t-butyl peroxybenzoate, t-butyl peroxyisobutyrate, t-butyl peroxy-2-ethylhexanoate, t-butyl peroxypivalate, t-butyl peroxyneoheptanoate, t-butyl peroxyneodecanoate, t-amyl peroxyacetate, t-amyl peroxy-3,5,5-trimethylhexanoate, t-amyl peroxybenzoate, t-amyl peroxyisobutyrate, t-amyl peroxy-2-ethylhexanoate, t-amyl peroxypivalate, t-amyl peroxyneoheptanoate, t-amyl peroxyneodecanoate, 1,1,3,3-tetramethylbutyl peroxy-2-ethylhexanoate, 1,1,3,3-tetramethylbutyl peroxypivalate, 1,1,3,3-tetramethylbutyl peroxyneoheptanoate, 1,1,3,3-tetramethylbutyl peroxyneodecanoate, 3-hydroxy-1,1-dimethylbutyl peroxy-2-ethylhexanoate, 3-hydroxy-1,1-dimethylbutyl peroxyneoheptanoate, 3-hydroxy-1,1-dimethylbutyl peroxyneodecanoate, 2,5-dimethyl-2,5-di(benzoylperoxy) hexane, 2,5-dimethyl-2,5-di-(2-ethylhexanoylperoxy) hexane, alpha-cumyl peroxyneoheptanoate and alpha-cumyl peroxyneodecanoate; diacyl peroxides such as dibenzoyl peroxide, didecanoyl peroxide, didodecanoyl peroxide and di-(3,5,5-trimethylhexanoyl) peroxide; peroxydicarbonates such as dipropyl peroxydicarbonate, di-(2-butyl) peroxydicarbonate, diisopropyl peroxydicarbonate, dicyclohexyl peroxydicarbonate, di-(4-t-butylcyclohexyl) peroxydicarbonate and di-(2-ethylhexyl) peroxydicarbonate; diperoxyketals such as 2,2-di-(t-butylperoxy)butane, 2,2-di-(t-butylperoxy)propane, 1,1-di-(t-butylperoxy) cyclohexane, 1,1-di-(t-butylperoxy)-3,3,5-trimethylcyclohexane, ethyl 3,3-di-(t-butylperoxy)butyrate, n-butyl 4,4-di-(t-butylperoxy)pentanoate, 2,2-di-(t-amylperoxy)butane, 2,2 -di-(t-amylperoxy) propane, 1,1-di-(t-amylperoxy) cyclohexane, 1,1-di-(t-amylperoxy)-3,3,5-trimethylcyclohexane, ethyl 3,3-di-(t-amylperoxy)butyrate and n-butyl 4,4-di-(t-amylperoxy)pentanoate; OO-t-alkyl O-alkyl monoperoxycarbonates such as OO-t-butyl O-isopropyl monoperoxycarbonate, OO-t-butyl O-(2-ethylhexyl) monoperoxycarbonate, OO-t-amyl O-isopropyl monoperoxycarbonate and OO-t-amyl O-(2-ethylhexyl) monoperoxycarbonate; dialkyl peroxides such as di-t-butyl peroxide, t-butyl alpha-cumyl peroxide, 2,5-dimethyl-2,5-di-(t-butylperoxy) hexane, 2,5-dimethyl-2,5-di-(t-butylperoxy)-3-hexyne, di-t-amyl peroxide, t-amyl alpha-cumyl peroxide and 2,5-dimethyl-2,5-di-(t-amylperoxy)hexane; and azo initiators such as azobis(isobutyronitrile).

The polymerization conditions used to homo- and copolymerize the novel unsaturated peroxides of Structure A will vary with the type of monomer used, but generally the conditions for a specific monomer will be similar to those known in the art. The only requirement is that the reaction temperatures, times, solvents, initiators, and catalysts are such that substantial degradation of the novel unsaturated peroxide or of the resulting polymeric peroxy containing recurring units does not occur.

Temperatures of about 0° C. to 250° C., preferably 20° C. to 200° C. and non-invention initiator levels of 0.002% to 3%, preferably 0.003% to 1% by weight based on polymerizable monomers, are normally employed for the homo- and copolymerizations of the novel unsaturated peroxides of Structure A to produce the novel polymeric peroxides of the second composition aspect of the invention.

The polymeric peroxides of the second composition aspect of the invention can also be prepared by initially homo- or copolymerizing an ethylenically unsaturated monomer which possesses a functional group that is reactive with hydroxy peroxides. The conditions for the homo- or copolymerization reactions are similar to those given above. Non-limiting examples of reactive monomers include acryloyl chloride, methacryloyl chloride, isocyanatoethyl methacrylate, 1-(1-isocyanato-1-methylethyl)-3-(1-methylethenyl)benzene and 1-(1-isocyanato-1-methylethyl)-4-(1-methylethenyl)benzene. The initially formed homo- or copolymers possess pendant reactive groups which subsequently are reacted with hydroxy peroxides to produce the novel polymeric peroxides of the second composition aspect of the invention. Examples of reactive hydroxy peroxides are given above. It should be noted that Example 16 illustrates this method.

PREPARATIVE EXAMPLES

The following examples further illustrate the best mode contemplated by the inventors for the practice of their invention, are presented to provide detailed preparative illustrations and are not intended to limit the scope of the present invention.

Example 1

Preparation of 1,3 -Dimethyl-3-(t-butylperoxy) butyl N-(1-{3-(1-Methylethenyl)phenyl)}-1-methyl-ethyl]carbamate (PM-1)

Reaction of 1,3-dimethyl-3-(t-butylperoxy)butanol with 1-(1-isocyanato-1-methylethyl)-3-(1-methylethenyl)benzene:

An Erlenmeyer flask was charged with 10 g of toluene, 12.0 g (57.0 mmoles) of 90.4% 1,3-dimethyl-3-(t-butylperoxy)butanol, 10.6 g (52.7 mmoles of 1-(1-isocyanato-1-methylethyl)- 3-(1-methylethenyl)benzene [TMI, manufactured by the American Cyanamid Company], and 0.1 g of dibutyltin dilaurate (catalyst). The flask was fitted with a reflux condenser and was placed in a 70° C. water bath, and the reaction mixture was stirred magnetically for 2 hours. The reaction mixture was then allowed to stand overnight (ca. 1.5 hours) at room temperature. The reaction mixture was then reheated to 60° C. to dissolve the precipitate that formed. Next, 10 mL of methanol was added and the reaction mixture was stirred for 0.5 hour. As much of the solvent as was possible was removed using a rotary evaporator. The resultant slurry was dissolved in hot hexane to form a clear solution. Upon cooling to −20° C. a white precipitate formed, which was suction filtered and dried to yield 18.1 g (87.9%) of a white powder, mp 68°–70° C. Analysis of the product by infrared spectroscopy (KBr) showed a strong carbonyl absorption at 1680 cm$^{-1}$ and the absence of an iscoyanate absorption at 2260 cm$^{-1}$. Analysis of the product by gas chromatography indicated that it contained less than 0.1% residual starting peroxide. A rapid heat test showed a peroxide decomposition at about 147° C.

Example 2

Preparation of 3-Methyl-3-(t-butylperoxy)butyl N-[1-{3-(1-Methylethenyl)phenyl}-1-methyl-ethyl]carbamate (PM-2)

Reaction of 3-methyl-3-(t-butylperoxy)butanol with 1-(1-isocyanatio-1-methylethyl)-3-(1-methylethenyl)benzene:

A process similar to that employed in Example 1 was used to prepare the title peroxy monomer (PM-2) via reaction of 3-methyl-3-(t-butylperoxy)butanol with TMI. A liquid product was obtained in a crude yield of 85%. Analysis of the product by infrared spectroscopy showed an NH band at about 3320 cm$^{-1}$, broad carbonyl absorption bands at 1720 cm$^{-1}$ and at 1690 cm$^{-1}$ and the absence of an isocyanate absorption band at 2260 cm$^{-1}$. Analysis by high performance liquid chromatography indicated that 4.5% residual starting peroxide [3-methyl-3-(t-butylperoxy)butanol]remained in the product. Analysis of the product by differential scanning calorimetry (DSC) showed a major peroxide decomposition exotherm at about 187° C.

The results of the above analyses and the method of preparation demonstrate that the desired titled peroxy monomer (PM-2) was the predominant component of the product produced in this example.

Example 3

Preparation of Di-[1,1-dimethyl-3-(1-{3 -(1-methylethenyl)}phenyl-1-methylethyl-aminocarbonyloxy-)butyl] Peroxide (PM-3)

Reaction of di-(3-hydroxy-1,1-dimethylbutyl) peroxide with 1-(1-isocyanato-1-methylethyl)-3-(1-methylethyl)benzene:

A process similar to that employed in Example 1 was used to prepare the title peroxy monomer (PM-3) via reaction of one mole of di-(3-hydroxy-1,1-dimethylbutyl) peroxide with two moles of TMI. A white solid product was obtained in a crude yield of 61%. The melting point was found to be 111°–114° C. Analysis of the product by infrared spectroscopy showed an NH band at about 3330 cm$^{-1}$, a carbonyl absorption band at 1680 cm$^{-1}$ and the absence of an isocyanate absorption band at 2260 cm$^{-1}$. Analysis by high performance liquid chromatography indicated that the purity of the product was about 92%. Analysis of the product by differential scanning calorimetry (DSC) showed a major peroxide decomposition exotherm at about 189° C.

The analysis results and the method of preparation demonstrated that the desired title peroxy monomer (PM-3) was the predominant component of the product produced in this example.

Example 4

Preparation of 1,3-Dimethyl-3-(2-methylbenzoylperoxy)butyl N-(1-{3-Methylethenyl)phenyl}-1-methylethyl]carbamate (PM-4)

Reaction of 3-hydroxy-1,1-dimethylbutyl peroxy-2-methylbenzoate with 1-(1-isocyanato-1-methylethyl)-3-(1-methylethenyl)benzene:

A 3-necked flask fitted with a thermometer and a reflux condenser was charged with 10.0 g (39.6 mmoles) of 3-hydroxy-1,1-dimethylbutyl peroxy-2-methylbenzoate, 8.0 g (39.7 mmoles) of TMI, 60 g of toluene, and 0.1 g of dibutyltin dilaurate. The reaction mixture was heated to 60° C. for 2 hours, whereupon another 0.1 g of dibutyltin dilaurate was added. After an additional 2 hours at 60° C., a sample of the reaction mixture was analyzed by infrared spectroscopy which showed that only a small isocyanate band remained. Then 10 mL of methanol was added, and the reaction mixture was stirred for 0.5 hour. Removal of the solvent using a rotary evaporator and a vacuum pump afforded 18.0 g (100%) of a viscous yellow oil. Analysis of the oil by infrared spectroscopy showed a large carbonyl band at 1725 cm$^{-1}$ and the absence of an isocyanate band at 2260 cm$^{31\ 1}$. Analysis by high performance liquid chromatography indicated that 8.6% residual starting peroxide remained.

The above results demonstrate that most of the starting peroxide reacted with the isocyanate to form the desired product.

Example 5

Preparation of 1,3 -Dimethyl-3-(t-amylperoxy) butyl N-[1-{3-(1-Methylethenyl)phenyl}-1-methylethyl]carbamate (PM-5)

Reaction of 1,3-dimethyl-3-(t-amylperoxy)butanol with 1-(1-isocyanato-1-methylethyl)-3-(1-methylethenyl)benzene:

A 3-necked flask which was fitted with a thermometer and a reflux condenser was charged with 50.0 g (234.9 mmoles) of 96% 1,3-dimethyl-3-(t-amylperoxy)butanol, 47.3 g (235.0 mmoles) of TMI, 60 g of toluene, and 1.0 g of dibutyltin dilaurate. The resultant solution was magnetically stirred and was heated in a 70° C. water bath for 2 hours. Analysis of a sample of the reaction mixture by infrared spectroscopy indicated that no isocyanate was present. The reaction mixture was diluted with 60 mL of methanol and was stirred for another 0.5 hour. As much of the solvent as was possible was removed using a rotary evaporator, and the resultant slurry was diluted with hexane, cooled to −20° C., and suction filtered. Obtained was 59.6 g (62.5%) of a white powder, mp 53°–55° C. An infrared spectrum (KBr) showed a strong carbonyl band at 1690 cm$^{-1}$ indicative of a carbamate and the absence of an isocyanate band at 2260 cm$^{-1}$.

The above results demonstrate that the desired title peroxide was formed.

Example 6

Preparation of Ethyl 1,3-Dimethyl-3-(t-butyl-peroxy)butyl Fumarate (PM-6)

Reaction of 1,3-dimethyl-3-(t-butylperoxy)butanol with trans-3-ethoxycarbonyl-2-propenoyl chloride (ethyl fumaryl chloride) in the absence and in the presence of common bases such as NaOH, KOH, $Na_2CO_3$, $KHCO_3$, $K_2CO_3$, triethylamine and other inorganic and organic bases failed to yield the desired titled product.

Surprisingly, a highly substituted urea, 1,1,3,3-tetramethylurea, was found to be an effective base for reaction of ethyl fumaryl chloride with 1,3-dimethyl-3-(t-butylperoxy)butanol. The synthetic procedure using 1,1,3,3-tetramethylurea as a base for preparing the titled peroxide (PM-6) is described below.

A 250 mL 3-neck flask equipped with a magnetic stirrer, a thermometer, a condenser and an addition funnel was charged with 100 mL of methyl t-butyl ether, 17.4 g (0.15 mole) of 1,1,3,3-tetramethylurea (TMU) and 14.7 g (0.07 mole) of 90.7% 1,3-dimethyl-3-(t-butylperoxy)butanol. To the resulting stirred solution at 21°–27° C. was slowly added 11.4 g (0.07 mole) of 100% trans-3-ethoxycarbonyl-2-propenoyl chloride (ethyl fumaryl chloride) over a period of 10 minutes. The resulting solution was then stirred for ca. 6 hours at 50° C. The solution was then poured into 100 mL of water and the methyl t-butyl ether layer was separated. The methyl t-butyl ether layer was then washed twice with 50 mL portions of aqueous 10% KOH solution and then with 50 mL portions of water until the pH was about 7. After drying over about 10% by weight of anhydrous $MgSO_4$ the spent desiccant was separated by filtration and the solvent was removed in vacuo leaving 18.6 g (84% of theory, uncorrected) of an amber liquid product. An infrared spectrum of the product showed a strong ester carbonyl band at ca. 1720 $cm^{-1}$ and a carbon-carbon double bond band at ca. 1640 $cm^{-1}$. A liquid chromatography scan showed a major peak which indicated ca. 92.5% product purity according to area percent. According to gas chromatography the product also contained ca. 5% of 1,3-dimethyl-3-(t-butylperoxy)butanol, one of the reactants. Based on liquid chromatographic purity the corrected yield for the product was ca. 78%.

Based on the method of preparation, yield data, infrared data and liquid chromatographic data the product obtained in this reaction was the desired titled product, ethyl 1,3-dimethyl-3-(t-butylperoxy) butyl fumarate (PM-6).

Example 7

Preparation of Di-[1,3-Dimethyl-3-(t-butylperoxy)butyl]Fumarate ( PM-7 )

Reaction of 1,3-dimethyl-3-(t-butylperoxy)butanol with fumaryl chloride in the absence and in the presence of common bases such as NaOH, KOH, $NaHCO_3$, $Na_2CO_3$, $KHCO_3$, $Na_2CO_3$, triethylamine and other inorganic and organic bases failed to yield the desired titled product.

1,1,3-3-Tetramethylurea, was found to be an effective base for reaction of fumaryl chloride with 1,3-dimethyl-3-(t-butylperoxy)butanol. The synthetic procedure using 1,1,3,3-tetramethylurea as a base for preparing the titled peroxide (PM-7) is described below.

A 250 mL 3-neck flask equipped with a magnetic stirrer, a thermometer, a condenser and an addition funnel was charged with 100 mL of methyl t-butyl ether, 28.0 g (0.24 mole) of 1,1,3,3-tetramethylurea (TMU) and 14.7 g (0.07 mole) of 90.7% 1,3-dimethyl-3-(t-butylperoxy) butanol. To the resulting stirred solution at 20°–25° C. was slowly added 5.6 g (0.035 mole) of 95% fumaryl chloride over a period of 10 minutes. The resulting solution was stirred for ca. 7.5 hours at 50°–60° C., then cooled to 20° C. and an additional 100 mL of methyl t-butyl ether was added to the reaction mass. The solution was then poured into 100 mL of water and the methyl t-butyl ether layer was separated. The methyl t-butyl ether layer was then washed twice with 50 mL portions of aqueous 5% KOH solution, then washed with a 50 mL portion of aqueous 3% hydrochloric acid solution and then with 50 mL portions of water until the pH was about 7. After drying over about 10% by weight of anhydrous $MgSO_4$ the spent desiccant was separated by filtration and the solvent was removed in vacuo leaving 13.6 g (84% of theory, uncorrected) of a light yellow liquid product. An infrared spectrum of the product showed a strong ester carbonyl band at ca. 1740 $cm^{-1}$ and a small carbon-carbon double bond band at ca. 1645 $cm^{-1}$. A liquid chromatography scan showed a major peak which indicated ca. 90% desired product and ca. 10% 1,3-dimethyl-3-(t-butylperoxy)butanol, one of the reactants. Based on the liquid chromatographic purity the corrected yield for the product was ca. 76%.

Based on the method of preparation, yield data, infrared data and liquid chromatorahpic data the product obtained in this reaction was the desired titled product, di-[1,3-dimethyl-3-(t-butylperoxy)butyl] fumarate (PM-7).

Example 8

Preparation of 1,3-Dimethyl-3-(t-butylperoxy)butyl Hydrogen Maleate (PM-8)

A 100 mL 3-neck flask equipped with a magnetic stirrer, a thermometer and a condenser was charged with 21.1 g (0.10 mole) of 90.7% 1,3-dimethyl-3-(t-butylperoxy) butanol, 12.5 g (0.125 mole) of maleic anhydride and 6 drops of aqueous 50% sulfuric acid solution. The stirred reaction mixture was then heated to and held at 55°–65° C. for about 6 hours after which the reaction mixture was cooled to room temperature and poured into 100 mL of water. The organic layer that resulted was extracted with 200 mL of methyl t-butyl ether and the methyl t-butyl ether solution was washed with 100 mL of water at 30°–35° C. The resulting solution was dried over about 10% by weight of anhydrous $MgSO_4$. The spent desiccant was separated by filtration and the solvent was removed in vacuo leaving 12.2 g (42% of theory, uncorrected) of a liquid product. An infrared spectrum of the product showed a small OH band, an anhydride carbonyl band at about 1785 $cm^{-1}$, a strong ester carbonyl band at ca 1740 $cm^{-1}$ and a carbon-carbon double bond band at ca. 1650 $cm^{-1}$. The product was then poured into 100 mL of aqueous 3% NaOH solution, stirred for 5 minutes at 20°–25° C. in order to prepare the sodium salt of the title product and to hydrolyze the excess maleic anhydride. The salt solution was extracted twice with 100 mL portions of pentane in order to remove neutral impurities. The salt solution was then brought to a pH of 2–3 with dilute hydrochloric acid solution and the resulting mixture was extracted twice with 100 mL portions of methyl t-butyl ether and the methyl t-butyl ether extracts were combined. The resulting solution was dried over about 10% by weight of anhydrous $MgSO_4$ the spent desiccant was separated by filtration and the solvent was removed in vacuo leaving 11.2 g (39% of theory, uncorrected) of a light yellow liquid product. A liquid chromatography scan showed a major peak which indicated ca. 96% product purity according to area percent. The liquid chromatography scan of the product also showed that it contained a minor amount of 1,3-dimethyl-3-(t-butylperoxy)butanol, one of the reactants. Based on the liquid chromatographic purity the corrected yield for the product was ca. 37%. Analysis of the product by differential scanning calorimetry (DSC) showed a major peroxide decomposition exotherm at about 170° C.

Based on the method of preparation, yield data, infrared data, liquid chromatographic data and DSC data the product obtained in this reaction was the desired title product, 1,3-dimethyl-3-(t-butylperoxy)butyl hydrogen maleate (PM-8).

Example 9

Preparation of 1,3-Dimethyl-3-(t-butylperoxy)butyl Methacrylate (PM-9)

A 300 mL 3-neck flask equipped with a magnetic stirrer, a thermometer, a condenser and an addition funnel was charged with 150 mL of methyl t-bdtyl ether, 19.8 g (0.25 mole) of . pyridine and 41.7 g (0.20 mole) of 92% 1,3-dimethyl-3-(t-butylperoxy)butanol. To the resulting stirred solution at 21°–27° C. was slowly added 24.4 g (0.21 mole) of 90% methacryloyl chloride over a period of 45 minutes. The resulting solution was then stirred for ca. 6 hours at 25°–30° C. after which the reaction mixture was poured into 300 mL of water and the methyl t-butyl ether layer was separated. The water layer was extracted with one 100 mL portion of methyl t-butyl ether. The combined portions of methyl t-butyl ether were then washed with a 150 mL portion of aqueous 5% HCl solution and then twice with 100 mL portions of aqueous 3% $NaHCO_3$ solution. After drying over about 10% by weight of anhydrous $MgSO_4$, the spent desiccant was separated by filtration and the solvent was removed in vacuo leaving 38.2 g (74% of theory, uncorrected) of a light yellow liquid product. An infrared spectrum of the product showed no OH band in the OH band region, a strong ester carbonyl band at ca. 1720 $cm^{-1}$ and a carbon-carbon double bond band at ca. 1640 $cm^{-1}$. According to gas chromatography the product also contained ca. 5% of 1,3-dimethyl-3-(t-butylperoxy)butanol, one of the reactants.

Based on the method of preparation, yield data and infrared data the product obtained in this reaction was the desired titled product, 1,3-dimethyl-3-(butylperoxy)butyl methacrylate (PM-9).

Example 10

Preparation of 1,3 -Dimethyl-3 -(t-butylperoxy)butyl Acrylate ( PM-10)

A process similar to that employed in Example 9 was used to prepare the title peroxy monomer (PM-10) via reaction of 1,3-dimethyl-3-(t-butylperoxy)butanol (0.266 mole) with acryloyl chloride (0.346 mole) in the presence of triethylamine (0.359 mole) and N-methylpyrrolidone (ca. 230 mL, reaction solvent). After isolation of the crude liquid product in 93% yield, the product was distilled at 48° C./0.1 torr., resulting in a 72.7% yield of colorless liquid. Analysis of the distilled product by infrared spectroscopy showed an ester carbonyl absorption band at 1722 $cm^{-1}$ and an olefinic band at 1620–1640 $cm^{-1}$. Analysis by high performance liquid chromatography showed only one peak. This indicated that the distilled product was of very high purity. Analysis of the product by differential scanning calorimetry (DSC) showed a major peroxide decomposition exotherm at about 186° C.

Based on the method of preparation, yield data, liquid chromatography data, DSC data and infrared data the product obtained in this reaction was the desired title product, 1,3-dimethyl-3-(t-butylperoxy)butyl acrylate (PM-10).

Example 11

Preparation of 1,3-Dimethyl-3-(t-butylperoxy)butyl TONE-100 Carbonate (PM-11)

In this reaction 1,3-dimethyl-3-(t-butylperoxy)butyl chloroformate was reacted with TONE-100 in the presence of triethylamine as a base. TONE-100 is a hydroxy acrylate monomer of the structure:

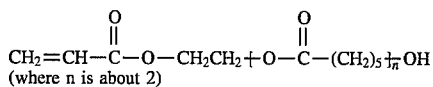

(where n is about 2)

manufactured by the Union Carbide Corporation. TONE-100 was initially dried by dissolving 13.3 g (37.8 mmoles) of TONE-100 in 75 mL of dry ethyl acetate, adding ca. 10% by weight of anhydrous $MgSO_4$, stirring, separating the spent desiccant by filtration and washing the spent desiccant with 25 mL of dry ethyl acetate. The combined ethyl acetate solution was added to a 300 mL 3-neck flask equipped with a magnetic stirrer, a thermometer, a condenser and an addition funnel. The 300 mL 3-neck flask was also charged with 0.1 g of p-N,N-dimethylaminopyridine (DMAP) and 5.7 g (56.3 mmoles) of triethylamine. To the resulting stirred solution at room temperature was slowly added 10.0 g (37.8 mmoles) of 96% 1,3-dimethyl-3-(t-butylperoxy)butyl chloroformate over a period of 15 minutes. The resulting reaction mixture was then stirred at room temperature for about 2 hours after which the reaction mixture was washed several times with aqueous 10% HCl solution and then once with 100 mL saturated aqueous $NaHCO_3$ solution. After drying over about 10% by weight of anhydrous $MgSO_4$ the spent desiccant was separated by filtration and the solvent was removed in vacuo leaving 20.8 g (96% of theory, uncorrected) of a light yellow liquid product. An infrared spectrum of the product, showed a small OH band centered at ca. 3500 $cm^{-1}$, a strong carbonate carbonyl band at ca. 1740 $cm^{-1}$, a strong ester carbonyl band at ca 1700 $cm^{-1}$, a weak carbon-carbon double bond band at ca. 1640 $cm^{-1}$ and an -OO- band at ca. 875 $cm^{-1}$. According to gas chromatography the product also contained ca. 6% 1,3-dimethyl-3-(t-butylperoxy) butanol, a hydrolysis product derived from 1,3-dimethyl-3-(t-butylperoxy)butyl chloroformate, one of the reactants.

Based on the method of preparation, yield data and infrared data, the product obtained in this reaction was the desired title product, 1,3-dimethyl-3-(t-butylperoxy) butyl TONE-100 carbonate (PM-11).

Example 12

Preparation of OO-t-butyl O-(TONE-100) Monoperoxycarbonate (PM-12)

In this reaction t-butyl hydroperoxide was reacted with TONE-100 chloroformate in the presence of NaOH (aqueous 10%) as a base. TONE-100 chloroformate was initially prepared in an assay of 93% and in a corrected yield of 51% by reacting TONE-100 with excess phosgene.

A 250 mL jacketed reactor equipped with a mechanical stirrer, a thermometer and an addition funnel was charged with 44.0 g (0.11 mole) of aqueous 10% NaOH solution and 10.0 g (0.10 mole) of 90% t-butyl hydroperoxide and the resulting solution was stirred for 5 minutes at 20°–25° C. To this vigorously stirred solution at 25°–30° C. was slowly added a solution of 32.2 g (0.072 mole) of 93% TONE-100 chloroformate in 100 mL of methyl t-butyl ether over a period of 20 minutes and the resulting reaction mass was stirred for 3 hours at 25°–32° C. Additional (50 mL) methyl t-butyl ether was added and stirring was stopped. A poor separation of liquid phases resulted. Solid $Na_2SO_4$ was added to aid the separation of the lower aqueous layer and the upper organic layer. The lower aqueous layer was removed and discarded. An additional 250 mL of methyl t-butyl ether was added and the organic layer was washed three times with 100 mL portions of aqueous 20% NaOH solution, then with one 100 mL portion of saturated aqueous $(NH_4)_2SO_4$ solution, then the resulting mixture was allowed to settle overnight. The lower aqueous layer was then removed and discarded. After drying over about 10% by weight of anhydrous $MgSO_4$ the spent desiccant was separated by filtration and the solvent was removed in vacuo leaving 28.7 g (85% of theory, uncorrected) of a clear viscous liquid product. The product had an active oxygen content of 2.40% (theory, 3.40%), therefore, the assay of the product according to active oxygen content was 71% and the corrected yield was 60%. Analysis of the product by differential scanning calorimetry (DSC) showed a peroxide decomposition exotherm at about 107° C.

Based on the method of preparation, yield data and DSC data the product obtained in this reaction was the desired title product, OO-t-butyl O-(TONE-100) monoperoxycarbonate (PM-12):

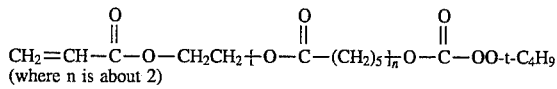
(where n is about 2)

Example 13

Preparation of 2-Methacryloyloxyethyl 3,3-Di-(t-butylperoxy) butyrate (PM-13)

A 500 mL jacketed reactor equipped with a mechanical stirrer, a thermometer and an addition funnel was charge with 39.9 g (0.19 mole) of 2-acetoacetoxyethyl methacrylate, 68.5 g (0.53 mole) of aqueous 70% t-butyl hydroperoxide solution and 7.0 g of granular ammonium sulfate and the resulting mixture was stirred for 5 minutes at room temperature. Stirring was stopped and the lower aqueous layer that formed (15.3 g) was removed and discarded. To the resulting vigorously stirred solution at 0°–3° C. was added 56.0 g of aqueous 70% sulfuric acid solution over a period of 10–15 minutes. Then the resulting mixture was vigorously stirred for 3 hours at 0°–3° C. At the end of the stir period a solid was present in the reaction mass, therefore, 400 mL of methylene chloride was added in order to dissolve the solid product and to aid in the work-up. Stirring was stopped and the resulting aqueous layer (70.5 g) was removed and discarded. The stirred product layer was then treated with 200 mL of 5% aqueous NaOH solution at 0°–5° C. for 5 minutes. The aqueous layer was removed and the latter wash procedure was repeated on the product. The product solution was then washed with 50 mL portions of water until the pH of the product was 7. The product solution was then dried over 28.4 g of anhydrous $MgSO_4$ and after removal of the spent desiccant by filtration the solvent was removed in vacuo leaving 61.3 g (86% of theory, uncorr.) of a light yellow oil which solidified on standing at room temperature. This product was recrystallized from 1/1 methanol/water and was dried. Obtained was 48.1 g (67% of theory, uncorr.) of white solid, mp, 35° C. The product had an active oxygen content of 9.14% (theory, 8.50%), therefore, the assay of the product according to active oxygen content was 100% and the corrected yield was 67%.

In another experiment in which the yield was considerably lower, the product had a melting point of 30°–5° C. and a rapid heat temperature of 132° C. During the rapid heat test the sample initially melted, then solidified before it decomposed at the rapid heat temperature. This observation showed that the product, 2-methacryloyloxyethyl 3,3-di-(t-butylperoxy)butyrate (PM-13), polymerized to a solid peroxy polymer prior to decomposing.

Based on the method of preparation, assay data and safety characteristics the product obtained from the reaction of this example was the desired title product, 2-methacryloyloxyethyl 3,3-di-(t-butylperoxy)butyrate (PM-13).

Example 14

Preparation of Di-(3-methacryloyloxy-1,1-dimethylbutyl) Peroxide (PM-14)

A 125 mL Erlenmeyer flask equipped with a magnetic stirring bar and a thermometer was charged with 4.7 g (0.020 mole) of 100% di-(3-hydroxy-1,1-dimethylbutyl) peroxide, 6.2 g (0.078 mole) of pyridine and 30 mL of methyl t-butyl ether. To this solution at room temperature was rapidly added a solution of 4.7 g (0.040 mole) of 90% methacryloyl chloride in 20 mL of methyl t-butyl ether over a period of 2 minutes. The reaction mass rapidly exothermed from 26° C. to 33° C. and a sticky white solid formed on the sides of the flask. After stirring for 90 minutes at room temperature the reaction mixture was allowed to stand overnight at room temperature. Then to the stirred reaction mass was added 50 mL of water and 25 mL of methyl t-butyl ether, and, after allowing the mixture to settle into two liquid phases, the lower aqueous layer was removed and discarded. The product solution was washed twice with 50 mL portions of 1.5% aqueous hydrochloric acid solution and then once with a 50 mL portion of saturated aqueous $NaHCO_3$ solution. The product solution was then dried over about 10% by weight of anhydrous $MgSO_4$ and after removal of the spent desiccant by filtration the solvent was removed in vacuo leaving 6.6 g (89% of theory, uncorr.) of a yellow liquid product. An infrared spectrum of the product showed a slight OH band centered at ca. 3500 $cm^{-1}$, a strong ester carbonyl band at ca. 1720 $cm^{-1}$, a carbon-carbon double bond band at ca. 1640 $cm^{-1}$ and a small -OO- band at ca. 870 $cm^{-1}$.

Based on the method of preparation, yield and infrared spectral data the product obtained from the reaction of this example was the desired title product, di-(3-methacryloyloxy-1,1-dimethylbutyl) peroxide (PM-14).

Example 15

Copolymerization of 1,3-Dimethyl-3-(t-butylperoxy)butyl N-[1-{3-(1-Methylethenyl)phenyl}-1-methylethyl]carbamate (PM-1) with Styrene to form a Peroxy Polymer (PP-1)

Copolymerization of the peroxy monomer of Example 1 (PM-1) with styrene:

A one-liter reactor was fitted with a nitrogen inlet line, a thermometer, a mechanical stirrer with a turbine impeller and a reflux condenser. The reactor was charged with 450 g of triply distilled water, 1.0 g calcium phosphate powder, and 0.75 g of polyvinyl alcohol. The aqueous suspension was sparged with nitrogen and was heated to 80° C. Then a solution of 144.0 g (1.38 moles) of styrene, 6.0 g (15.3 mmoles) of the peroxy monomer of Example 1 (PM-1), 0.8 g (2.1 mmoles) of 50% t-amyl peroxypivalate and 0.4 g (1.7 mmoles) of 98% t-amyl peroxy-2-ethylhexanoate (LUPERSOL 554-M50 and LUPERSOL 575, respectively, both manufactured by ELF ATOCHEM North America, Inc.) was added to the reactor. The reaction mixture was stirred between 400–600 rpm at 80° C. for 2 hours and then at 90° C. for 4 hours. The reaction mixture was cooled to room temperature, acidified to a pH of 1 with 20–25 mL of 10% HCl, and suction filtered. The filter cake was washed with deionized water until a pH 6 was attained. After drying 140.9 g (93.9%) of polystyrene copolymer was obtained. An infrared spectrum of the product was essentially identical to one for polystyrene except that there was an additional peak of moderate intensity at 1730 $cm^{-1}$ for the carbonyl group derived from the peroxy monomer. The molecular weight distribution as determined by size exclusion gel permeation chromatography was as follows: Mn, 60,000; Mw, 275,000; Mz, 715,000. Analysis by high performance liquid chromatography showed that there was 0.4% residual starting peroxy monomer (PM-1) present. If no copolymerization occurred the residual peroxy monomer (PM-1) would be about 4%. To insure that no peroxy monomer (PM-1) was present, a 7.0 g sample of the copolymer was dissolved 40 mL of xylene at 60° C. The resultant solution was added slowly to a vigorously stirred solution of methanol (methanol to xylene 10:1) in order to precipitate the copolymer and to wash out any residual peroxy monomer (PM-1). The resulting copolymer was then washed with fresh methanol and was subsequently dried. Analysis of the precipitated and methanol washed copolymer by differential scanning calorimetry showed a peroxide decomposition peak with an onset temperature of 186° C.

The above results demonstrate that a peroxy monomer of this invention (PM-1) can be copolymerized with a co-monomer to form a peroxy polymer (PP-1) and that the peroxide function is indeed chemically attached to the peroxy copolymer (PP-1) since it was not lost by dissolving, reprecipitating and methanol washing of the resulting copolymer.

Example 16

Terpolymerization of Methyl Methacrylate, Allyl Methacrylate and 1-(1-Isocyanato-1-methylethyl)-3-(1-methylethenyl)benzene to form an Acrylic Terpolymer with Pendant Reactive Isocyanato Groups followed by Reaction with 3-Hydroxy-1,1-dimethylbutyl Peroxy-2-ethylhexanoate to form a Peroxy polymer (pp-2) with Pendant Peroxyester Groups A 1.5 liter jacketed glass reactor that was fitted with a mechanical stirrer, a thermometer, a nitrogen sparge line, a reflux condenser and a monomer feed line was charged with 340 g of methyl ethyl ketone. The solvent was sparged with nitrogen and was heated to 75° C. A monomer/initiator feed consisting of 18 g (0.143 mole) of allyl methacrylate, 158.1 g of (1.58 moles) of methyl methacrylate, 69.9 g (0.269 mole) of TMI and 12.0 g (0.0346 mole) of di-(sec-butyl) peroxydicarbonate (LUPERSOL 225, manufactured by ELF ATOCHEM North America, Inc.) was metered into the hot solvent at a rate of 5.2 g/min. During the first hour of the reaction the reaction temperature was 66° C. due to cooling caused by the monomer feed. Subsequently, the temperature rose to 69° C. After a total reaction time of 220 minutes, a 1.0 mL aliquot of the clear reaction solution was withdrawn and was added to pentane to precipitate the polymer. An infrared spectrum (Nujol mull) of the resulting polymer showed a strong isocyanate band at 2290 cm$^{-1}$. To the acrylic copolymer reaction solution was added 69.6 g (0.269 mole) of 3-hydroxy1,1-dimethylbutyl peroxy-2-ethylhexanoate (LUPERSOL 665, manufactured by ELF ATOCHEM North America, Inc.) and 6.0 g of dibutyltin dilaurate. After the reaction mixture was stirred at 60° C. for 90 minutes, an additional 3.0 g of dibutyltin dilaurate was added. After another 90 minutes, an infrared spectrum of the resultant polymer showed the complete absence of the isocyanate band, showing that the pendant isocyanato groups of the acrylic terpolymer had completely reacted with 3-hydroxy-1,1-dimethylbutyl peroxy-2-ethylhexanoate to form an acrylic terpolymer (i.e., PP-2) with pendant peroxyester groups.

This example illustrated an alternate procedure for the preparation of a peroxy polymer. It also demonstrated the reaction of a suitably functionalized peroxide with a polymer possessing pendant isocyanato groups to form a peroxy polymer.

Example 17

Copolymerization of 1,3-Dimethyl-3-(t-butylperoxy)butyl Acrylate (PM-10) with Styrene to form a Peroxy Polymer (PP-3)

Copolymerization of the peroxy monomer of Example 10 (PP-10) with styrene to form a peroxy polymer (PP-3):

The polymerization reactor employed in this example was a Parr, 2-liter stirred stainless steel pressure vessel with a Model 4843 temperature controller. The stirring shaft was equipped with two six-bladed stainless steel impellers positioned approximately 5 cm apart on the shaft. The stir speed was held constant at about 460 rpm.

The above reactor was charged at room temperature with 46 g of 1% aqueous Airvol™ 540 (manufactured by Air Products Corp.) solution, 2.3 g of 0.1% aqueous Emulphogene™ BC-840 (manufactured by GAF Corp.) surfactant solution, 415 g of deionized water, 266.8 g (2.56 moles) of styrene monomer (inhibited), 8.25 g (0.034 mole) of 1,3-dimethyl-3-(t-butylperoxy)butyl acrylate (PM-10), 0.73 g of t-amyl peroxypivalate and 0.62 g of 2,5-dimethyl-2,5-di-(2-ethylhexanoylperoxy)hexane (LUPERSOL 256, manufactured by ELF ATOCHEM North America, Inc.). The reactor was then purged with nitrogen, sealed and pressurized with nitrogen to 20 psi. The time-temperature profile employed in the vigorously stirred copolymerization reaction was as follows:

a) Warm to 70° C.

b) 70° C. for 60 minutes.

c) 75° C. for 60 minutes.

d) 90° C. for 180 minutes.

e) 95° C. for 65 minutes.

f) Cool to room temperature.

The reaction vessel was then vented and the resulting suspended copolymer was acidified with aqueous HCl and diluted with 150 g of ice water. The resulting polymer was separated from the aqueous slurry by filtration and the resulting wet polymer was washed several times with water after which the polymer beads were dried overnight on a large paper tray. Approximately 254 g of white polymer beads was obtained after drying. The active oxygen content of the product peroxy copolymer (PP-3) was 0.12% (theory, 0.20%). The peroxy copolymer molecular weights were as follows:

$M_n$—92,000

$\bar{M}_w$—300,000

$\bar{M}_z$—688,000

DSC showed that the product peroxy copolymer had a $T_g$ of about 98° C. and a peroxide decomposition exotherm at about 201° C. An infrared spectrum of the product showed a small ester carbonyl band at about 1720 cm$^{-1}$. Except for this band the infrared spectrum of the product peroxy copolymer was exactly the same as that of the authentic polystyrene.

The above results for the analyses of the product copolymer demonstrate that the desired title peroxy polymer (PP-3) was successfully prepared by the method of this example.

Example 18

Crosslinking Efficiency of 1,3 -Dimethyl-3-t-butylperoxy) butyl N-[1-{3-(1-Methylethenyl)phenyl}-1-methylethyl] carbamate (PM-1) in High Density Polyethylene (HDPE).

The appropriate amount of peroxide was compounded into high density polyethylene (HDPE, produced by U.S. Industrial Chemical, grade LY66000) using a Brabender Plastograph at 140° C. for 5 min. The crosslinking was measured using a Monsanto Rheometer run at 385° F. and 3° arc. Employed as crosslinking peroxides were 1,3-dimethyl-3-(t-butylperoxy)butyl N-[1-{3-(1-methylethenyl)phenyl}-1-methylethyl]carbamate (PM-1, a peroxy monomer of the instant invention) and two commercially employed crosslinking peroxides, i.e., 2,5-dimethyl-2,5-di-(t-butylperoxy) hexane and 2,5-dimethyl-2,5-di-(t-butylperoxy)-3-hexyne (LUPERSOL 101 and LUPERSOL 130, respectively, both manufactured by ELF ATOCHEM North America, Inc.). The following crosslinking results were obtained for use of 10 meq. of peroxide per 100 g of HDPE:

| Formulation | A | B | C |
| --- | --- | --- | --- |
| PM-1 (phr) (Example 1) | 3.91 | | |
| LUPERSOL 101 (phr) | | 1.45 | |
| LUPERSOL 130 (phr) | | | 1.43 |
| $M_H$ (in-lbs) | 62 | 38 | 45 |
| $M_H$-$M_L$ (in-lbs) | 60 | 35 | 44 |
| $T_{C90}$ (mins) | 4.5 | 4.6 | 8.1 |
| $T_{S2}$ (mins) | 1.4 | 1.2 | 1.6 |

The $M_H$–$M_L$ results demonstrate that PM-1, the peroxy monomer of Example 1, is an effective crosslinking agent for HDPE when compared with commerically available crosslinking agents such as LUPERSOL 101 and LUPERSOL 130. Yet its use results in a reasonably short cure time ($T_{C90}$) and a reasonably long scorch safety time ($T_{S2}$).

Example 19

Crosslinking Efficiency of 1,3-Dimethyl-3-(t-butylperoxy)butyl Methacrylate (PM-9) in High Density Polyethylene (HDPE)

1,3-Dimethyl-3-(t-butylperoxy)butyl methacrylate (PM-9) was evaluated for crosslinking efficiency in HDPE compared to 1,3-dimethyl-3-(t-butylperoxy)butanol and 2,5-dimethyl-2,5-di-(t-butylperoxy)-3-hexyne (LUPERSOL 130). PM-9, 1,3-dimethyl-3-(t-butylperoxy)butanol and LUPERSOL 130, at appropriate levels, were blended into HDPE (USI's LY 66000 HDPE) at 140° C. using a Brabender mixer. Disks of the compounded HDPE resins were pressed out and these resin disks were used for determining crosslinking data using a Monsanto Oscillating Disk Rheometer (ODR) at 385° F., ±3° arc. The crosslinking data obtained are summarized in the table below:

| CROSSLINKING OF HDPE AT 385 deg. F. (196 deg. C.) | | | | | |
| --- | --- | --- | --- | --- | --- |
| FORMULATION: | A | B | C | D | E |
| LUPERSOL 130 (phr) | 1.43 | — | — | — | — |
| 1,3-Dimethyl-3-(t-butylperoxy)-butanol (phr) | — | 1.43 | 1.93[1] | — | — |
| PM-9 (phr) | — | — | — | 1.43 | 2.58[1] |
| $M_H$ (in-lbs) | 41 | 19.5 | 24.5 | 25 | 43.5 |
| $M_H$-$M_L$ (in-lbs) | 40 | 17.8 | 22.8 | 24 | 42.5 |
| $T_{C90}$ (mins) | 11.1 | 4.5 | 4.4 | 6.0 | 5.5 |
| $T_{S2}$ (mins) | 1.85 | 1.45 | 1.35 | 2.3 | 2.0 |

[1]Level equivalent in peroxide content to LUPERSOL 130 at 1.43 phr.
[2]All sample levels corrected for assay.

These data demonstrate that PM-9, a peroxy monomer of the instant invention, is much more efficient than 1,3-dimethyl-3-(t-butylperoxy)butanol and is as efficient a crosslinking agent for HDPE as the commercial product LUPERSOL 130 when employed at an equivalent peroxide basis as judged by change in torque data. In addition, PM-9 gave faster cures of HDPE than the commerical product LUPERSOL 130 as judged by $T_{C90}$ data. Finally, and surprisingly, PM-9 was somewhat less scorchy than was the commerical product LUPERSOL 130 as judged by $T_{S2}$ data. Consequently, the results showed that PM-9, a peroxy monomer of the instant invention, was a very good crosslinking peroxide candidate for HDPE.

Example 20

Copolymerization of 1,3-Dimethyl-3-(t-butylperoxy)butyl Acrylate (pM-10) with Methyl Methacrylate to form a Peroxy Polymer (pp-4 )

copolymerization of the peroxy monomer of Example 10 (PM-10) with methyl methacrylate to form a peroxy polymer (PP-4):

The polymerization reactor employed in this vessel was a Parr 2-liter stirred stainless steel pressure vessel with a Model 4843 temperature controller. The stirring shaft was equipped with two six-bladed stainless steel impellers positioned approximately 5 cm apart on the shaft. The stirring speed was held constant at about 470 rpm.

The above reactor was charged at room temperature with about 50g of 1% aqueous Airvol™ 540 (manufactured by Air Products Corp.) solution, 2.0 g of 0.1% aqueous Emulphogene™ BC-840 (manufactured by GAF Corp.) surfactant solution and 590 g of deionized water. Then a solution of 188 g (1.88 moles of methyl methacrylate monomer, 12.0 g (0.05 mole) of 1,3-dimethyl-3-(t-butylperoxy)butyl acrylate (PM-10) and 1.02 g of 98% di-(2-butyl) peroxydicarbonate (LUPERSOL 225, manufactured by ELF ATOCHEM North America, Inc.) was added to the reactor. The reactor was then purged with nitrogen, sealed, pressurized with nitrogen to 20 psi (137.9 kPa) and stirring was started. The time temperature profile in the vigorously stirred copolymerization reaction was as follows:

a) warm to 65° C., b) 65° C. for 30 minutes, c) 70° C. for 120 minutes, d) 75° C. for 60 minutes, e) cool to room temperature (24° C.).

The reaction vessel was then vented and opened. To the resulting polymer slurry was added 100 g of ice and the slurry was stirred. The copolymer was separated from the aqueous slurry by filtration and the resulting wet product was washed several times with water. The copolymer was slurried in methanol, filtered and dried overnight on a large paper tray. Approximately 190 g of white beads of the title peroxy copolymer product (PP-4) was obtained after drying. The active oxygen content of the peroxy copolymer was 0.37% (theory, 0.39%), the methyl methacrylate monomer level was 0.21% and the peroxy monomer level was 0.09%. copolymer molecular weights were as follows:

$\bar{M}_n$—87,600

$\bar{M}_w$—320,000

$\bar{M}_z$—720,000

Thermomechanical analysis (TMA) showed that the product peroxy copolymer (PP-4) had a $T_g$ of about 97° C. whereas poly(methylmethacrylate) had a $T_g$ of about 105° C.

The above results for the analyses of the product copolymer demonstrate that the desired title proxy copolymer (PP-4) was successfully prepared by the method of this example.

Example 21

Preparation of 1,3-Dimethyl-3-(acetylperoxy)butyl N-[1-(3-(1-Methylethenyl)phenyl)-1-methylethyl]carbamate (PM-15)

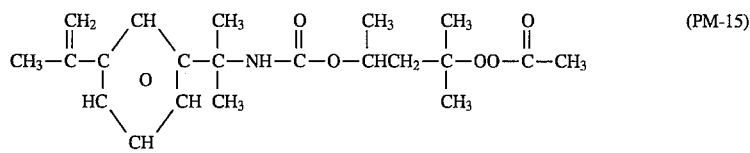

Reaction of 3-hydroxy-1,1-dimethylbutyl peroxyacetate with 1-1(1-isocyanato-1-methylethyl)-3-(1-methylethenyl)benzene (TMI):

A 200-mL 3-neck flask equipped with a magnetic stirrer, a thermoneter, and a condenser was charged with about 10 g of methyl t-butyl ether, 5.0 g (27.0 mmoles) of 94.8% 3-hydroxy-1,1-dimethylbutyl peroxyacetate, 5.0 g (25 mmoles) of TMI, and 0.1 g of dibutyltin dilaurate (catalyst). The contents of the flask were stirred and held at 55°–60° C. for 9 hours. An infrared spectrum of the reaction mass still showed the presence of TMI as judged by a significant isocyanate band at $cm^{-1}$. The reaction mass was stirred at 25° C. for 14 hours, then at 55°–60° C. for 4 hours. An infrared spectrum of the reaction mass at this point indicated that little or no TMI was present. The reaction mixture was then cooled to 30° C., 5 mL of methanol was added and the reaction mixture was stirred for 0.5 hour. As much of the solvent as was possible was removed using a rotary evaporator. To the resulting paste was added 100 mL of pentane, the solid was separated by filtration and the pentane was removed using a vacuum rotary evaporator. The solid-liquid residue was added to 100 mL of hexane, the mixture was heated to 55° C., and the hexane solution was separated from the solid by decantation. Hexane was removed using a vacuum rotary evaporator, leaving 4.7 g (50% of theory, uncorrected) of a clear liquid product. A liquid chromatography scan of the product showed that it contained 1.6% of starting 3-hydroxy-1,1-dimethylbutyl peroxyacetate. The peroxyester active oxygen content of the product was 3.99% (theory, 4.24%). Based on corrected peroxyester active oxygen content, the assay of the product was 90.7% and the corrected yield was 45.3%. Analysis of the product by infrared spectroscopy showed a strong carbonyl absorption at 1725 $cm^{-1}$ with a shoulder at about 1770 $cm^{-1}$, and the absence of an isocyanate absorption at about 2250 $cm^{-1}$.

Example 22

Preparation of 1,3-Dimethyl-3-(isobutyrylperoxy)butyl N-[1-{3-(1-Methylethenyl)phenyl}phenyl}-1-methylethyl]carbamate (PM-16)

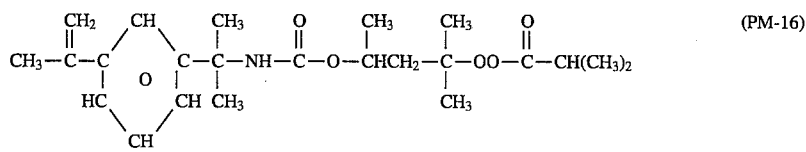

Reaction of 3-hydroxy-1,1-dimethylbutyl peroxyisobutyrate with 1-(1-isocyanato-1-methylethyl)-3-(1-methylethenyl)benzene (TMI):

A 200-mL 3-neck flask equipped with a magnetic stirrer, a thermometer, and a condenser was charged with about 10 g of methyl t-butyl ether, 5.9 g (27.0 mmoles) of 93.8% 3-hydroxy-1,1-dimethylbutyl peroxyisobutyrate, 5.0 g (25 mmoles) of TMI, and 0.1 g of dibutyltin dilaurate (catalyst). The contents of the flask were stirred and held at 55°–60° C. for 9 hours. An infrared spectrum of the reaction mass still showed the presence of TMI as judged by a significant isocyanate band at 2250 $cm^{-1}$. The reaction mass was stirred at 25° C. for 14 hours, then at 55°–60° C. for 3 hours. An infrared spectrum of the reaction mass at this point indicated that little or no TMI was present. The reaction mixture was then cooled to 35° C., 5 mL of methanol was added and the reaction mixture was stirred for 20 minutes. As much of the solvent as was possible was removed using a rotary evaporator and the solid that remained in the liquid was separated by filtration. To the resulting liquid was added 100 mL of pentane, the solution was cooled to 0° C. to 5° C., the solid that precipitated was separated by filtration and the pentane was removed using a vacuum rotary evaporator. Obtained was 7.8 g (77% of theory, uncorrected) of a yellow liquid product. A liquid chromatography scan of the product showed that it contained 1.1% of starting 3-hydroxy-1,1-dimethylbutyl peroxyisobutyrate. The peroxyester active oxygen content of the product was 3.73% (theory, 3.95%). Based on corrected peroxyester active oxygen content, the assay of the product was 92.2% and the corrected yield was 71.2%. Analysis of the product by infrared spectroscopy showed a strong carbonyl absorption at 1725 $cm^{-1}$ and 1770 $cm^{-1}$, and absence of an isocyanate absorption at about 2250 $cm^{-1}$.

The subject matter which applicants regard as their invention is particularly pointed out and distinctly claimed as follows:

We claim:

1. An ethylenically unsaturated peroxide of Structure A:

$$R-Q-X-R_1 \qquad A$$

where:

Q is an unsaturated diradical selected from structures (1), (2) or (3):

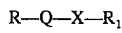

(1)

-continued

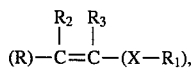

(2)

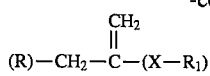 (3)

where —(X—R₁) shows the point of attachment of the X—R₁ group and (R)— shows the point of attachment of the R group to the Q diradical;

R is selected from the group consisting of H—, carboxy, alkoxycarbonyl radicals of 2 to 19 carbons, aryloxycarbonyl radicals of 7 to 15 carbons, t-alkylperoxycarbonyl radicals of 5 to 11 carbons, alkyl radicals of 1 to 18 carbons, alkenyl radicals of 2 to 18 carbons, aryl radicals of 6 to 10 carbons, and R₁—X— radicals;

R₂ is selected from the group consisting of H— and alkyl radicals of 1 to 4 carbons;

R₃ is selected from the group consisting of H—, alkyl radicals of 1 to 18 carbons and alkenyl radicals of 2 to 18 carbons, provided that when R₃ is methyl, R and R₂, are not both hydrogen;

R₁ is a peroxy-containing radical of structures (4), (5) and (6):

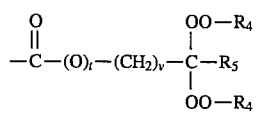 (4)

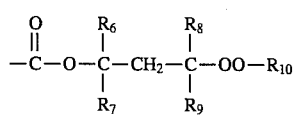 (5)

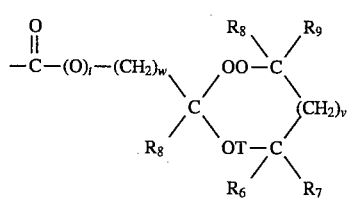 (6)

where t is 0 or 1;
v is 1 or 2;
w is 1 or 2;

T is a direct bond or oxy; R₄ is selected from the group consisting of t-alkyl radicals of 4 to 12 carbons, t-aralkyl radicals of 9 to 13 carbons and t-alkynyl radicals of 5 to 9 carbons;

R₅, R₆ and R₉ are the same or different and are selected from the group consisting of alkyl radicals of 1 to 4 carbons; in structure (5) and when T is a direct bond in structure (6), R₆ and R₇ are the same or different and are selected from the group consisting of H— and alkyl radicals of 1 to 4 carbons; in structure (6) when T is oxy, R₆ and R₇ are the same or different and are selected from the group consisting of alkyl radicals of 1 to 4 carbons;

R₁₀ is selected from the group consisting of t-alkyl radicals of 4 to 12 carbons, t-aralkyl radicals of 9 to 13 carbons, t-alkynyl radicals of 5 to 9 carbons, and structures (7), (8), (9), (10), (11) and (12):

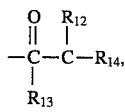 (7)

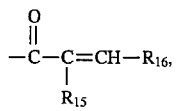 (8)

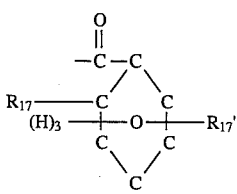 (9)

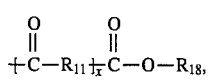 (10)

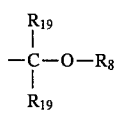 (11)

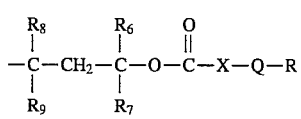 (12)

where:

R₁₂ and R₁₃ can be the same or different and are selected from the group consisting of H— and alkyl radicals of 1 to 8 carbons;

R₁₄ is selected from the group consisting of H—, alkyl radicals of 1 to 8 carbons, alkenyl radicals of 2 to 8 carbons, aryl radicals of 6 to 10 carbons, alkoxy radicals of 1 to 6 carbons and aryloxy radicals of 6 to 10 carbons;

R₁₃ and R₁₄ may be concatenated to form an alkylene diradical of 4 to 5 carbons;

R₁₅ and R₁₆ are independently selected from alkyl radicals of 1 to 4 carbons;

R₁₇ and R'₁₇ are independently selected from the group consisting of H— lower, alkyl radicals of 1 to 4 carbons, alkoxy radicals of 1 to 4 carbons, phenyl radicals, acyloxy radicals of 2 to 8 carbons, t-alkylperoxycarbonyl radicals of 5 to 9 carbons, hydroxy, fluoro, chloro and bromo;

x is 0 or 1;

R₁₈ is selected from substituted or unsubstituted alkyl radicals of 1 to 18 carbons, substituted or unsubstituted cycloalkyl radicals of 5 to 12 carbons, substituted or unsubstituted heterocyclic radicals having an oxygen atom or a nitrogen atom in the heterocyclic ring, with substituents for the alkyl radicals being one or more alkyl radicals of 1 to 6 carbons, t-alkylperoxy radicals of 4 to 8 carbons, alkoxy radicals of 1 to 6 carbons, aryloxy radicals of 6 to 10 carbons, hydroxy, chloro, bromo and cyano and with substituents for either cyclic radical being one or more lower alkyl radicals of 1 to 4 carbons, or R₁₈ is the radical:

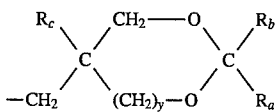

where y is 0 or 1,

R_a, R_b and R_c are the same or different and are selected from H— or alkyl radicals of 1 to 8 carbons, with the proviso. that $R_a$ and $R_b$ may be concatenated to form a substituted or unsubstituted alkylene diradical of 4 to 11 carbons, substituents being one or more alkyl radicals of 1 to 5 carbons or phenyl radicals;

$R_{19}$ is selected from the group consisting of alkyl radicals of 1 to 4 carbons and, additionally, the two $R_{19}$ radicals may optionally be concatenated to form an alkylene diradical of 4 to 5 carbons;

$R_{11}$ is selected from the group consisting of unsubstituted alkylene diradicals of 2 to 3 carbons, alkylene diradicals of 2 to 3 carbons substituted with one or more lower alkyl radicals of 1 to 4 carbons, a 1,2-phenylene diradical, 1,2-phenylene diradicals substituted with one or more lower alkyl radicals of 1 to 4 carbons, chloro, bromo, nitro or carboxy; and, X is a direct bond or is selected from the group consisting of connecting diradical structures (13), (14), (15) and (16):

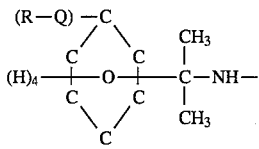

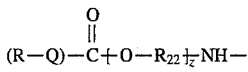

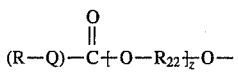

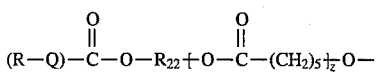

where (R—Q) shows the point of attachment of the R—Q group to the unsymmetrical X connecting diradical;

z is 1 to 10;

$R_{22}$ is an alkylene diradical of 2 to 4 carbons, optionally substituted with one or more alkyl radicals of 1 to 4 carbons; and, when the X connecting diradical is structure (16), $R_1$ may additionally be the peroxide containing radical of the structure (17):

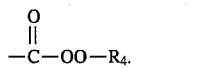

2. A peroxide as defined in claim 1 selected from the group consisting of:

1,3-Dimethyl-3-(t-butylperoxy)butyl N-[1-{3-(1-methylethenyl)phenyl}-1-methylethyl]carbamate, 3-methyl-3-(t-butylperoxy)butyl N-[1-{3-(1-methylethenyl)phenyl}-1-methylethyl]carbamate, di-[1,1-dimethyl-3-(1-{3-(1-methylethenyl)}phenyl-1-methylethylaminocarbonyloxy)butyl]peroxide, 1,3-dimethyl-3-(2-methylbenzoylperoxy)butyl N-[1-{3-(1-methylethenyl)phenyl}-1-methylethyl]carbamate, 1,3-dimethyl-3-(acetylperoxy)butyl N-[1-{3-(1-methylethenyl)phenyl}-1-methylethyl]carbamate, 1,3-dimethyl-3-(isobutyrylperoxy)butyl N-[1-{3-(1-methylethenyl)phenyl}-1-methylethyl]carbamate, 1,3-dimethyl-3-(t-amylperoxy)butyl N-[1-{3-(1-methylethenyl)phenyl}-1-methylethyl]carbamate, ethyl 1,3-dimethyl-3-(t-butylperoxy)butyl fumarate, di-[1,3-dimethyl-3-(t-butylperoxy)butyl]fumarate, 1,3-dimethyl-3-(t-butylperoxy)butyl hydrogen maleate, 1,3-dimethyl-3-(t-butylperoxy)butyl methacrylate, 1,3-dimethyl-3-(t-butylperoxy)butyl acrylate, 1,3-dimethyl-3-(t-butylperoxy)butyl TONE-100 carbonate, OO-t-butyl O-(TONE-100)monoperoxycarbonate, 2-methacryloyloxyethyl 3,3-di-(t-butylperoxy)butyrate and di-(3-methacryloyloxy-1,1-dimethylbutyl)peroxide.

3. A peroxide as defined in claim 1 wherein X is structure (13) as defined in claim 1.

4. A peroxide as defined in claim 1 wherein X is a direct bond.

5. A peroxide as defined in claim 1 wherein X is structure (16).

6. A peroxide as defined in claim 1 wherein X is structure (15).

7. A peroxide as defined in claim 1 wherein $R_1$ is structure (5).

8. A peroxide as defined in claim 1 wherein $R_1$ is structure (17).

9. A peroxide as defined in claim 1 wherein $R_1$ is structure (4).

10. A peroxide as defined in claim 1 wherein $R_{10}$ is structure (12).

11. A peroxide as defined in claim 1 wherein Q is structure (1) wherein R, $R_2$ and $R_3$ are H—.

12. A peroxide as defined in claim 1 wherein Q is structure (1) wherein R is alkoxycarbonyl, $R_2$ and $R_3$ are H—.

13. A peroxide as defined in claim 1 wherein Q is structure (3) wherein R is H—.

14. A peroxide as defined in claim 1 wherein Q is structure (1) wherein R is $R_1$—X—, $R_2$ and $R_3$ are H—.

* * * * *